United States Patent [19]

Clark et al.

[11] Patent Number: 5,340,829
[45] Date of Patent: Aug. 23, 1994

[54] IMMUNOREGULATORY AGENTS

[75] Inventors: John I. Clark; Andrew G. Farr, both of Seattle, Wash.; Stacia A. Smith, San Diego, Calif.

[73] Assignee: Washington Research Foundation, Seattle, Wash.

[21] Appl. No.: 990,571

[22] Filed: Dec. 15, 1992

Related U.S. Application Data

[63] Continuation of Ser. No. 309,446, Feb. 10, 1989, Pat. No. 4,966,911, which is a continuation-in-part of Ser. No. 159,357, Feb. 23, 1988, abandoned, which is a continuation of Ser. No. 6,985, Jan. 27, 1987, abandoned, which is a continuation of Ser. No. 673,534, Nov. 20, 1984, abandoned.

[51] Int. Cl.$^5$ .............................. A01N 43/50
[52] U.S. Cl. .................................... 514/389
[58] Field of Search ............................ 574/389

[56] References Cited

U.S. PATENT DOCUMENTS

| | | | |
|---|---|---|---|
| 4,127,665 | 11/1978 | Sarges et al. | 424/273 R |
| 4,130,714 | 12/1978 | Sarges | 548/309 |
| 4,147,795 | 4/1979 | Sarges | 424/273 R |
| 4,147,797 | 4/1979 | Kelbaugh et al. | 424/273 R |
| 4,181,728 | 1/1980 | Sarges et al. | 424/273 R |
| 4,181,729 | 1/1980 | Sarges et al. | 424/273 R |
| 4,235,911 | 11/1980 | Sarges | 424/258 |
| 4,248,882 | 2/1981 | Sarges et al. | 424/273 R |
| 4,286,098 | 8/1981 | Sarges | 548/309 |
| 4,348,526 | 9/1982 | Sarges | 548/309 |
| 4,431,828 | 2/1984 | Cue, Jr. et al. | 549/401 |
| 4,966,911 | 10/1990 | Clark et al. | 514/385 |

FOREIGN PATENT DOCUMENTS

256629 2/1988 European Pat. Off. .

OTHER PUBLICATIONS

Kador, P. F., et al., Anti-allergy drugs as aldose reductase inhibitors, *Invest. Ophthalmol. Visual Sci.*, 1980, Suppl. p. 12.

Smith, S. A., et al., An aldose reductase inhibitor inhibits inflammation, *Clin. Res.*, 34(2):507A, Apr. 1986.

Smith, S. A., et al., An aldose reductase inhibitor inhibits inflammation, *Clin. Res.*, 34(1):48A, 1986.

Cerelli, M. J., et al., Anti-inflammatory and aldose reductase inhibitory activity of some tricyclic arylacetic acids, *J. Med. Chem.*, 29:2347-2351, 1986.

Kador, P. F., et al., Aldose reductase inhibition by anti-allergy drugs, in Enzymology of Carbonyl Metabolism: Aldehyde Dehydrogenase and Aldo/Keto Reductase, Weiner, H., et al., eds., pp. 243-259, Alan R. Liss, N.Y., 1982.

Kador, P. F., and N. E. Sharpless, Pharmacophor requirements of the aldose reductase inhibitor site, *Molecular Pharmacology* 24:521-531, 1983.

Kissinger, C. R., et al., Crystal structure of sorbinil, $C_{11}H_9FN_2O_3$, *Acta Cryst.* C41:988-990, 1985.

Varughese, K. I., et al., The crystal structure of N-[[-6-methoxy-5-(trifluoromethyl)thio-1-naphthalenyl]-thioxomethyl]-N-methylglycine, $C_{16}H_{14}F_3NO_3S_2$, *Can. J. Chem.* 61:2137-2140, 1983.

Kissinger, C. R., et al., Structure of WF-3681, 3-2,-5-Dihydro-4-hydroxy-5-oxo-3-phenyl-2-furyl)propionic acid, *Acta Cryst.* C44:512-514, 1988.

(List continued on next page.)

*Primary Examiner*—Paul J. Killos
*Attorney, Agent, or Firm*—Christensen, O'Connor, Johnson & Kindness

[57] ABSTRACT

Specific aspects of the cellular and humoral immune systems of a mammalian host are regulated by administering to the host a compound having a reactive immunoregulatory conformation whose precise three-dimensional structure is defined herein. Sorbinil, tolrestat, W-3681, and the other immunoregulatory agents described herein possess this reactive conformation and so are therapeutically useful for inhibiting delayed-type hypersensitivity, T-cell proliferation, and B-cell antibody production, without altering the normal cellularity of the immune system or the normal metabolites of the arachidonic acid pathway.

4 Claims, 11 Drawing Sheets

OTHER PUBLICATIONS

Hall, P. C., and K. L. Keim, Anticonvulsant activity of sorbinil and AL-1576: hydantoin-containing aldose reductase inhibitors, *Federation Proceedings* 46(3):433, 606A, 1987.

Kador, P. F., et al., Differences in the susceptibility of various aldose reductases to inhibition, *Docum. Ophthal. Proc. Series* 18:117-124, 1979.

Kador, P. F., et al., Sterospecific inhibition of aldose reductase, *Eur. J. Med. Chem-Chimica Therapeutica* 16(4):293-298, 1981.

Yue, D. K., et al., The effect of aldose reductase inhibition on motor nerve conduction velocity in diabetic rats, *Diabetes* 31:789-794, 1982.

Sharma, Y. R., and E. Cotlier, Inhibition of lens and cataract aldose reductase by protein-bound anti-rheumatic drugs: salicylate, indomethacin, oxyphenbutazone, sulindac, *Exp. Eye Res.* 35:21-27, 1982.

Cogan, D. G., et al., Aldose reductase and complications of diabetes, *Annals of Internal Medicine* 101:82-91, 1984.

Research may alleviate diabetes complications, C&EN:5, 1983.

Kador, P. F., et al., Aldose reductase inhibitors: a potential new class of agents for the pharmacological control of certain diabetic complications, *J. Med. Chem.* 28(7):842-849, Jul. 1985.

Eaton, R. P., et al., The effect of an aldose reductase inhibiting agent on limited joint mobility in diabetic patients, *JAMA* 253(10):1437-1440, Mar. 1985.

Hicks, D. R., et al., Tolrestat kinetics, *Clin. Pharmacol. Ther.* 36(4):493-499, Oct. 1984.

IMMUNOREGULATORY AGENTS

This application is a continuation of international application No. PCT/US90/03618, filed Jun. 26, 1990, which is a continuation of Ser. No. 07/309,446, filed Feb. 10, 1989 (U.S. Pat. No. 4,966,911), which is a continuation-in-part of Ser. No. 07/159,357, filed Feb. 23, 1988 (abandoned), which is a continuation of Ser. No. 07/006,985, filed Jan. 27, 1987 (abandoned), which is a continuation of Ser. No. 06/673,534, filed Nov. 20, 1984 (abandoned).

TECHNICAL FIELD

This invention relates to therapeutic agents and more particularly to immunoregulatory agents.

BACKGROUND OF THE INVENTION

The enzyme aldose reductase catalyzes the reduction of glucose to sorbitol and has been implicated in processes leading to certain complications of diabetes, including cataracts, retinopathy, nephropathy, and peripheral neuropathy. For this reason, inhibitors of the aldose reductase enzyme are of considerable medical interest. For current reviews, see: Dvornik, D., Aldose Reductase Inhibition, McGraw-Hill, New York, N.Y., 1987; and, Polyol pathway and its role in diabetic complications, N. Sakamoto, et al., eds., Elsevier Science Publishers, New York, N.Y., 1988.

One of the strongest known aldose reductase inhibitors (ARI) is sorbinil, [4(S)-2,3-dihydro-6-fluorospiro-(4H-1-benzopyran-4,4'-imidazolidine)-2',5'-dione]. Sorbinil and its analogs, defined herein as spirohydantoin derivatives wherein essentially planar benzene and hydantoin rings are connected via a nonplanar pyran ring, are the subject of the following United States patents, all of which are herein incorporated by reference: U.S. Pat. Nos. 4,127,665; 4,130,714; 4,147,795; 4,147,797; 4,181,728; 4,181,729; 4,235,911; 4,286,098; 4,248,882; 4,348,526; and 4,431,828.

Other aldose reductase inhibitors whose molecular structures do not conform to the above-stated definition of sorbinil analogs are also known: tolrestat, N-[[6-methoxy-5-(trifluoromethyl)thio-1-napthalenyl]thioxomethyl]-N-methylglycine; flavonoids having the basic structure of 3-hydroxyflavone; acetylsalicylic acid (aspirin); diphenylhydantoin (Dilantin TM); phenobarbital; sulindac; indomethacin; ICI 105552; alrestatin (AY-22,284); and WF-3681, 3-(2,5-dihydro-4-hydroxy-5-oxo-3-phenyl-2-furyl)propionic acid.

The mechanism whereby sorbinil, sorbinil analogs, and other aldose reductase inhibitors inhibit the activity of the aldose reductase enzyme is unknown, as are the precise structural features that are important to that inhibition. It is known generally that the effect of a drug such as sorbinil depends upon the interaction of the drug molecule with its receptor site, which in this case is considered to be on the aldose reductase molecule. The most important factor in that interaction is the drug molecule's conformation, meaning the three-dimensional spatial arrangement of its atoms and groups, which positions interactive atoms in their most active three-dimensional geometry with respect to the complementary conformation of the receptor site. Interactive atoms are defined as those that may participate directly in chemical mechanisms that include charge-transfer, hydrogen bonding, electrophilic and/or nucleophilic substitutions, and hydrophobic interactions. Interacting atoms include but are not limited to oxygen, sulfur, and nitrogen. The active conformation of aldose reductase inhibitors has been hypothesized from theoretical modeling of molecular orbital calculations. For aldose reductase inhibitory activity the hypothesis identifies two important structural features: an aromatic ring or ring complex (for hydrophobic interaction with the receptor site) and an associated carbonyl group. The carbonyl may be $C=O$, as in sorbinil, or $C=S$ as in tolrestat. Kador, P. F., et al., in Enzymology of Carbonyl Metabolism: Aldehyde Dehydrogenase and Aldo/Keto Reductase, Weiner, H., et al., eds., pp. 243–259, A. R. Liss, New York, 1982; Kador, P. F., et al., Molecular Pharmacology 24: 521–531, 1983.

Precise molecular conformations, as determined by X-ray crystallography studies, have been published for only six aldose reductase inhibitors: 3-hydroxyflavone, aspirin (acetylsalicylic acid), phenobarbital, diphenylhydantoin (Dilantin), sorbinil (Kissinger, C. R., et al., Acta Cryst. C41: 988–990, 1985), tolrestat (Varughese, K. I., et al., Can. J. Chem. 61: 2137–2140, 1983), and WF-3681 (Kissinger, C. R., Acta Cryst. C44: 512–514, 1988).

Some of the aldose reductase inhibitors were known to also act as anti-inflammatory (AI) agents: flavonoids having the structural backbone as in 3-hydroxyflavone, acetylsalicylic acid, sulindac, and indomethacin. Two aldose reductase inhibitors were known to also act as anti-convulsant (AC) agents: diphenylhydantoin and phenobarbital.

The foregoing status of the published art is summarized in TABLE 1, which was tabulated for the purpose of illustrating the present invention. In the Table, six aldose reductase inhibitors for which the molecular conformation had been determined are listed in the left column. The center column lists the $IC_{50}$ which is the approximate molar concentration of compound necessary for 50% inhibition of aldose reductase. The Table shows that the $IC_{50}$ values range from $10^{-8}$ to $10^{-3}M$. The right column lists other pharmacological activities, either anti-inflammatory or anti-convulsant activity, that were known for some of these compounds.

TABLE 1

| Aldose Reductase Inhibitors | Approximate $IC_{50}$ (Molar) | Additional Pharmacological Activity |
|---|---|---|
| Sorbinil | $10^{-8}$ | (unknown) |
| Aspirin | $10^{-4}$ | Anti-inflammatory |
| Hydroxyflavone | $10^{-6}$ | Anti-inflammatory |
| Diphenylhydantoin | $10^{-4}$ | Anti-convulsant |
| Phenobarbital | $10^{-3}$ | Anti-convulsant |
| Tolrestat | $10^{-8}$ | (unknown) |

SUMMARY OF THE INVENTION

Pursuant to the present invention, certain aspects of the cellular and humoral immune systems of a mammalian host are specifically regulated by administering to the host a compound having a reactive immunoregulatory conformation whose precise three-dimensional structure is defined below. Sorbinil, tolrestat, WF-3681, and the other immunoregulatory agents described herein possess this reactive conformation and so are therapeutically useful for inhibiting delayed-type hypersensitivity, T-cell proliferation, and B-cell antibody production, without altering the normal cellularity of the immune system or the normal metabolites of the arachidonic acid pathway.

DESCRIPTION OF THE PREFERRED EMBODIMENT

The invention is predicated upon applicants' discovery that the mammalian immune system can be therapeutically perturbed in a previously undisclosed manner, by a family of compounds having a reactive conformation whose precise three-dimensional structure is defined below. These immunoregulatory agents do not affect the normal cellularity of the immune system in an unstimulated animal, but only regulate an immune system that is stimulated by pathological conditions. Such regulation includes inhibition of the delayed-type hypersensitivity (DTH) reaction, inhibition of T-cell mitogen responsiveness, and inhibition of antibody production in response to antigenic challenge. Notably, these effects are achieved without altering, in unstimulated animals, the normal metabolites of the arachidonic acid pathway. It is particularly noteworthy that the described regulatory effects are achieved when the subject compounds are administered either before or after the host's immune system is pathologically stimulated.

The subject compounds can be used to regulate specific aspects of the immune system, by inhibiting delayed-type hypersensitivity, T-cell proliferation, and B-cell antibody production. As such, these compounds are of therapeutic value in the treatment of autoimmune diseases, including periodontal disease and rheumatoid arthritis, allergic reactions, inflammatory dermatitis, hypersensitivity reactions, inflammation, undesirable side effects of immunization, graft rejection, and graft vs. host complications occurring in bone marrow transplantation.

Figure 1:
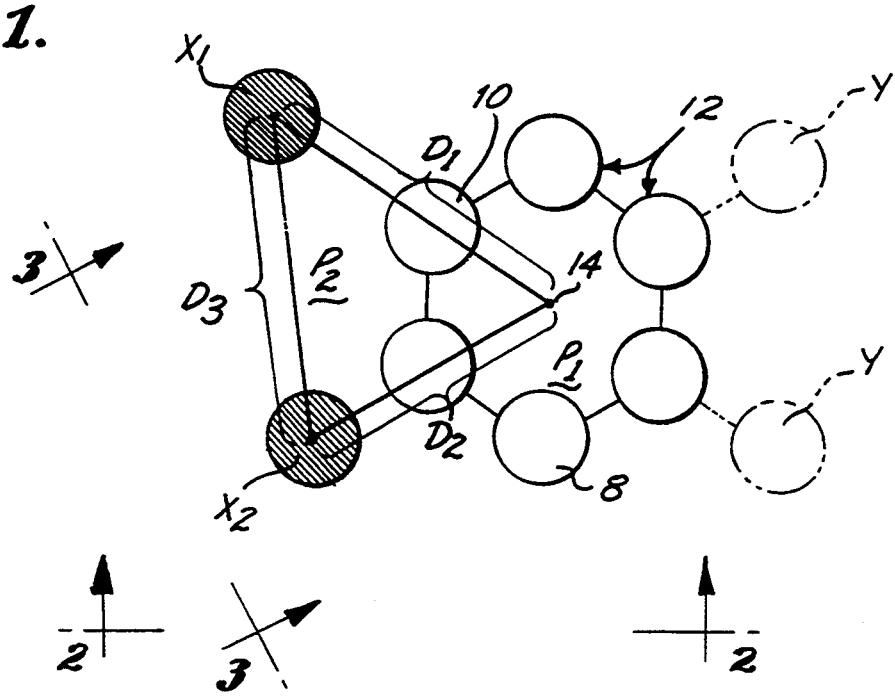
FIG. 1 is a diagrammatic frontal view of the immunoregulatory conformation, with plane $P_1$ parallel to the plane of projection.

The precise structure of the reactive conformation that characterizes the subject immunoregulatory agents is defined below with references to FIGS. 1–3. Referring to FIG. 1, an aromatic ring 12 is associated in defined conformation with two distinct interactive atoms $X_1$, $X_2$. The aromatic ring 12 is essentially planar, being composed of five to seven atoms (a representative six-membered ring is shown) that are cylindrically symmetrical within about 15 degrees of planar and preferably within about seven degrees or less of planar. The aromatic ring 12 can be homocyclic or heterocyclic. Representative rings 12 include benzene, pyridine, furan, and thiophene. Aromatic ring 12 may be part of a ring complex, e.g., a naphthalene or anthracene derivative. The interactive atoms $X_1$, $X_2$ can each be an oxygen, sulphur, or nitrogen atom. Each interactive atom $X_1$, $X_2$ may be a substituent of a hydantoin ring, ether, or other group that disposes the interactive atom in the defined conformation. The aromatic ring 12 (or ring complex) may have fluorine, chlorine, bromine, alkyl (having preferably 1 to 7 and most preferably 1 to 3 carbon atoms), and/or aromatic substituents Y that contribute to the structural stability, solubility, electronegative charge distribution, and steric properties of the compound without altering the defined conformation that imparts the distinctive immunoregulatory activity.

The reactive conformation of the subject immunoregulatory compounds can be defined with reference to the following parameters:

$P_1$ = the plane defined by the aromatic ring 12,
$P_2$ = the plane defined by the two interactive atoms $X_1$, $X_2$ and the center 14 of the aromatic ring 12, $D_1$ = the distance between the center 14 of the aromatic ring 12 and the nucleus of one of the interactive atoms $X_1$, $D_2$ = the distance between the center 14 of the aromatic ring 12 and the nucleus of the other interactive atom $X_2$, $D_3$ = the distance between the interactive atoms $X_1$, $X_2$, and $\alpha°$ = the angle between the planes $P_1$ and $P_2$, taken at the $\alpha°$ intersection of vectors constructed normal to each plane $P_1$, $P_2$.

The reactive conformation of the immunoregulatory compound is defined with respect to the aforementioned parameters as follows:

$$3.1 \text{ Å} \leq D_1 \leq 4.1 \text{ Å}$$

$$2.4 \text{ Å} \leq D_2 \leq 2.8 \text{ Å}$$

$$3.8 \text{ Å} \leq D_3 \leq 4.2 \text{ Å},$$

and $$35° \leq \alpha° \leq 60°.$$

Figure 2:
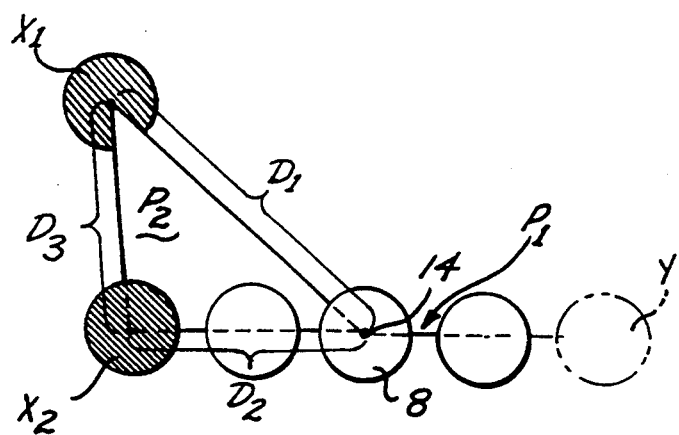
FIG. 2 is a diagrammatic edge view in which the immunoregulatory conformation shown in FIG. 1 has been rotated so that plane $P_1$ is perpendicular to the plane of projection, and so that reference atom 8 is projected toward the viewer.

Referring to FIG. 2, another view of the above-defined reactive conformation is shown, here in edge view in which FIG. 1 has been rotated so that plane $P_1$ is perpendicular to the plane of projection, and so that reference atom 8 of the aromatic ring 12 is projected toward the viewer.

Figure 3:
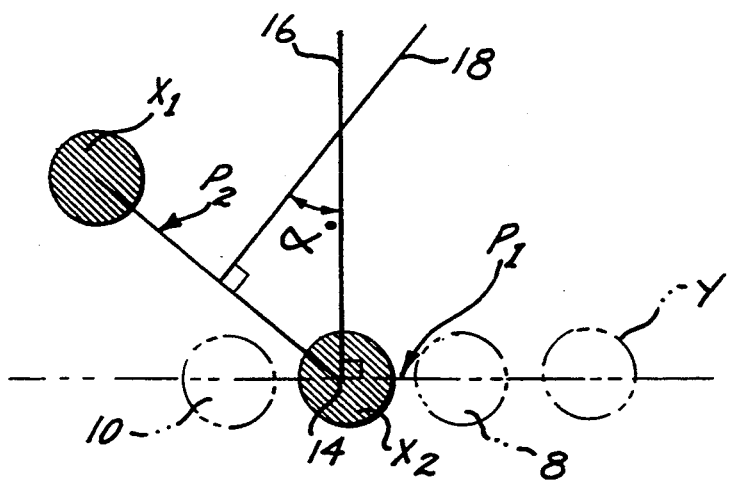
FIG. 3 is a diagrammatic edge view in which the immunoregulatory conformation shown in FIG. 2 has been rotated so that both of planes $P_1$ and $P_2$ are perpendicular to the plane of projection, and so that both of reference atoms 8, 10 are projecting toward the viewer.

Referring to FIG. 3, the angular relationship, $\alpha°$, between planes $P_1$ and $P_2$ is illustrated, here in edge view in which FIG. 2 has been rotated so that both of planes $P_1$ and $P_2$ are perpendicular to the plane of projection, and so that both of reference atoms 8, 10 of the aromatic ring 12 are projecting toward the viewer.

In a preferred embodiment, exemplified by sorbinil, the immunoregulatory compound has a reactive conformation that is defined with reference to FIGS. 1, 2, and 3 and the aforementioned parameters as follows:

$D_1$ equals approximately 4.06 Å,
$D_2$ equals approximately 2.74 Å,
$D_3$ equals approximately 4.00 Å, and
$\alpha°$ equals approximately 38.85°.

In another preferred embodiment, exemplified by tolrestat, the immunoregulatory compound has a reactive conformation that is defined as follows:

$D_1$ equals approximately 3.16 Å,
$D_2$ equals approximately 2.70 Å,
$D_3$ equals approximately 4.15 Å, and
$\alpha°$ equals approximately 59.0°.

In a third preferred embodiment, exemplified by WF-3681, the subject immunoregulatory compound has a reactive conformation that is defined as follows:

$D_1$ equals approximately 3.97 Å,
$D_2$ equals approximately 2.45 Å,
$D_3$ equals approximately 4.10 Å, and
$\alpha°$ equals approximately 47.0°.

TABLE 2 summarizes the relationship between the precise three-dimensional molecular structures of sorbinil, tolrestat, and WF-3681, and their unique immunoregulatory properties.

TABLE 2

| Compound, Activity | "Other" Activity | Reactive Conformation | $D_1$ (Å) | $D_2$ (Å) | $D_3$ (Å) | $\alpha°$ |
|---|---|---|---|---|---|---|
| Sorbinil ARI | IR AC | $P_1$—$O_1$—$O_{15}$ $P_1$—$O_1$—$O_{16}$ | 4.06 5.72 | 2.74 2.74 | 4.00 6.41 | 38.85 9.89 |
| Aspirin ARI | AI | Deacetylated $P_1$—$O_1$—$O_3$ Acetylated $P_1$—$O_3$—$O_4$ | 3.64 3.55 | 2.78 2.78 | 4.21 2.32 | 0.69 86.87 |
| Hydroxy-flavone ARI | AI | | 3.68 | 2.74 | 4.05 | 0.69 |
| Diphenyl-hydantoin ARI | AC | | 4.23 | No $X_2$ | No $X_2$ | No $P_2$ |
| Pheno-barbital ARI | AC | | 4.26 | No $X_2$ | No $X_2$ | No $P_2$ |
| Tolrestat ARI | IR | $P_1$—$S_2$—$O_2$ | 3.16 | 2.70 | 4.15 | 59.0° |
| WF-3681 ARI | IR | $P_1$—$O_2$—$O_4$ | 3.97 | 2.45 | 4.10 | 47.0° |

The left two columns of TABLE 2 list seven aldose reductase inhibitors (ARI) and their ocher pharmaceutical activities: anti-inflammatory (AI), anti-convulsant (AC), and immunoregulatory (IR) as defined herein; the underlined activities are pursuant to this disclosure. The coordinates and parameters of the immunoregulatory conformation are presented in the five right columns. For sorbinil, two values are listed for $D_1$, the distance between the center 14 of $P_1$ and interactive atom $X_1$, because sorbinil has two oxygens ($O_{15}$ and $O_{16}$ in FIGS. 4, 5, and 12) that could potentially participate in aldose reductase inhibitory activity. Aspirin also has two carbonyl oxygens ($O_1$ and $O_4$ in FIGS. 6, 7, 8, and 9) that could participate in aldose reductase inhibitory as well as anti-inflammatory activity. It is well known that aspirin is deacetylated to salicylate, and thereby loses one of the carbonyl oxygens ($O_4$), when administered clinically. TABLE 2 thus includes structural parameters for both the acetylated and deacetylated forms of aspirin. The flavone structure listed is 3-hydroxyflavone. Several flavonoid analogs are known to exhibit anti-inflammatory activity, and all of them have the same basic three-dimensional conformation as 3-hydroxyflavone. Both diphenylhydantoin and phenobarbital lack interactive atom $X_2$ and so are not encompassed by the disclosed immunoregulatory model. The reactive conformation coordinates of tolrestat and WF-3681 are described with reference to formulas 1 and 2 below.

Briefly stated, our analysis of the data of TABLE 2 can be summarized as follows:

1. aldose reductase inhibitory activity depends upon the presence of an aromatic ring 12 and an interactive atom $X_1$ in a carbonyl group, as was hypothesized in the prior art;
2. anti-convulsant activity of several aldose reductase inhibitors is associated with the presence of a hydantoin ring that contains the interactive atom $X_1$ that is associated with the aromatic ring 12;
3. anti-inflammatory and immunoregulatory activities of certain aldose reductase inhibitors are specifically determined by a conformational relationship between an aromatic ring 12, an interactive atom $X_1$ in a carbonyl group, and a second interactive atom $X_2$, all three of which define a plane $P_2$ with a specific spatial and angular orientation to the plane $P_1$ of the aromatic ring 12; and 4. the immunoregulatory compounds are distinguished from the anti-inflammatory compounds by having the defined reactive conformation.

With regard to anti-inflammatory and anti-convulsive activities, we recognize that an interactive atom $X_2$ is present in anti-inflammatory compounds and either absent or present in anti-convulsant compounds. In TABLE 2 the values for $D_2$, the distance between the center 14 of $P_1$ and $X_2$, have a narrow range (2.74 Å$<D_2<$2.78 Å) in the anti-inflammatory compounds. Note that no $D_2$ can be calculated for the anti-convulsant compounds that do not possess interactive atom $X_2$.

In the anti-inflammatory compounds, interactive atoms $X_1$ and $X_2$ are separated by distances $D_3$ that are also tabulated in TABLE 2. The interactive atoms $X_1$ and $X_2$ form a second plane, $P_2$, with the center 14 of plane $P_1$. The angular relationship between planes $P_1$ and $P_2$ is described by the angle, $\alpha°$, between vectors 16, 18 constructed normal to each of planes $P_1$ and $P_2$ (see FIG. 3). These values for alpha are also listed in TABLE 2.

With regard to the two anti-inflammatory compounds known in the prior art, aspirin and hydroxyflavone, a comparison of the $D_1$ values suggests that either the acetylated or deacetylated form of the aspirin can account for aldose reductase inhibitory activity. However, the data for $D_2$, $D_3$, and $\alpha°$ reveal interesting and potentially important structural differences that can be correlated with anti-inflammatory activity. For our purposes we concentrate on the deacetylated conformation of aspirin (FIGS. 6 and 7) because it is recognized that this form predominates over the acetylated form in vivo. Thus, the deacetylated aspirin (salicylate) and hydroxyflavone have $D_2=2.78$ Å and 2.74 Å, $D_3=4.21$ Å and 4.05 Å, and $\alpha°$ values of 0.69° and 0.69°, respectively. These parameters indicate that the reactive sites in aspirin and hydroxyflavone have very similar three-dimensional conformations. In contrast, the two potential reactive sites in sorbinil are distinctly different: $D_2=2.74$ for either, while $D_3$ equals 4.00 Å or 6.41 Å, and $\alpha°$ equals 38.85° or 9.89°, respectively.

Figure 4:
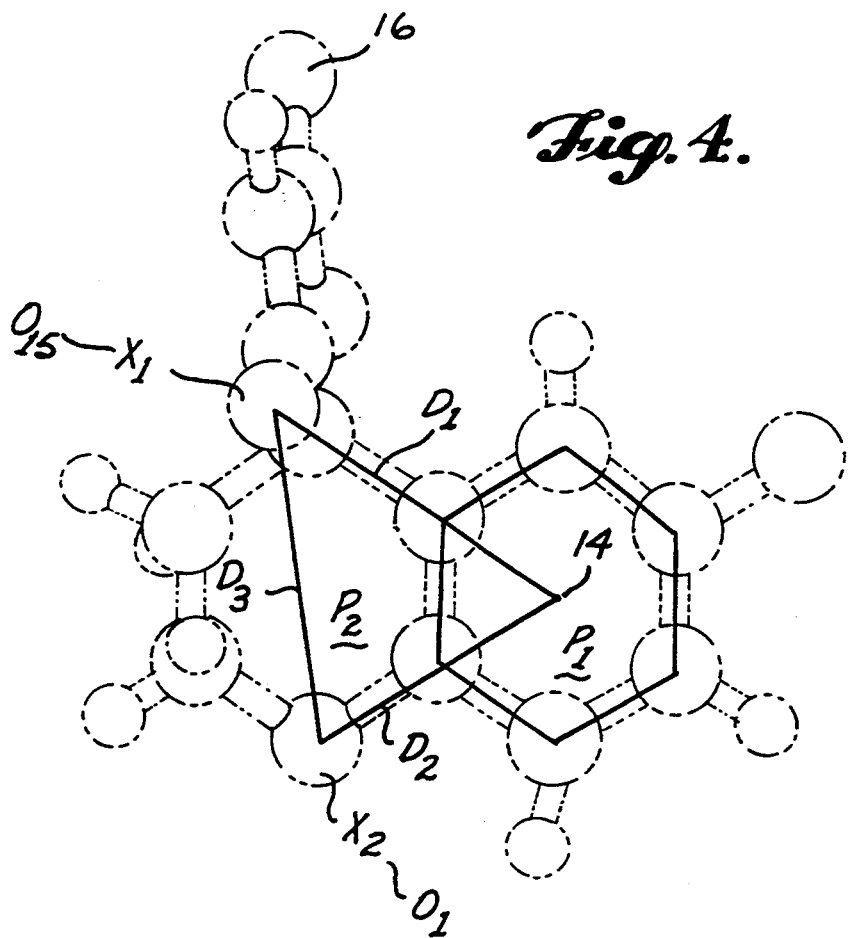
FIG. 4 depicts the immunoregulatory conformation of FIG. 1 superimposed upon the molecular conformation of sorbinil.
Figure 5:
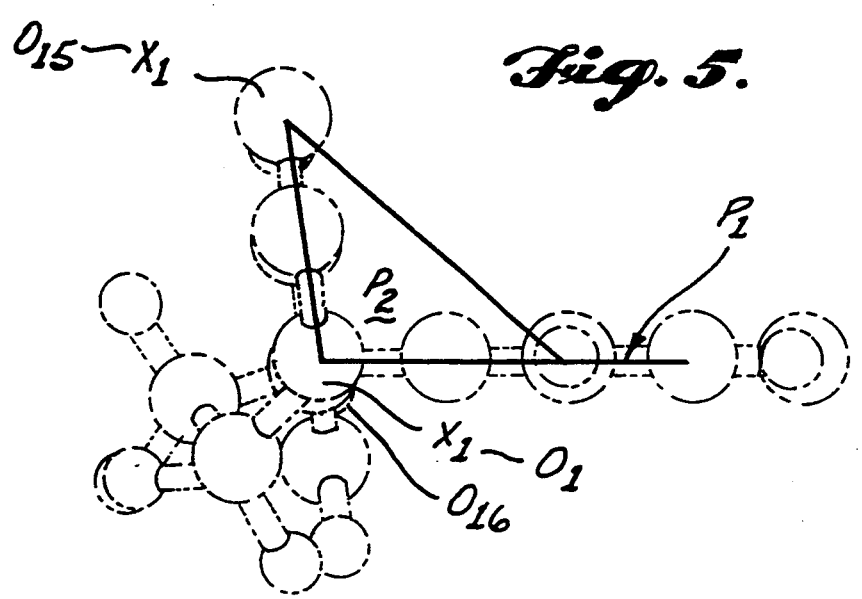
FIG. 5 depicts the immunoregulatory conformation of FIG. 2 superimposed upon the molecular conformation of sorbinil.

As shown in FIGS. 4 and 5, sorbinil has two carbonyl oxygens, $O_{15}$ and $O_{16}$, that may participate in the active conformation. The $D_1$ for $O_{15}$ is 4.06 Å, and the $D_1$ for $O_{16}=5.72$ Å. Note that $O_{16}$ is outside but $O_{15}$ is within the range of $D_1$ values for the other ARI compounds. TABLE 2 also demonstrates that $\alpha°$ for the $P_2$ of $O_{16}$ is much less than the a for the $P_2$ of $O_{15}$. We therefore conclude that $O_{15}$ is the active atom in sorbinil. $O_{15}$ has $D_2=2.74$ Å, $D_3=4.00$ Å which is very close to $D_3$ for deacetylated aspirin and hydroxyflavone, but the plane $P_2$ that includes $O_{15}$ has $\alpha=38.85°$. The similarities between the three-dimensional molecular structures of sorbinil, deacetylated aspirin, and hydroxyflavone led us to propose that sorbinil may exhibit anti-inflammatory in addition to aldose reductase inhibitory activity. Moreover, the dissimilarity in the $\alpha°$ values suggested that the nature of anti-inflammatory activity of sorbinil might be different than that of the other agents.

FIGS. 4 through 11 depict the molecular conformations for sorbinil and the aldose reductase inhibitors that have anti-inflammatory activity. Note that the model represented in FIGS. 1 and 2 is superimposed over the molecular structures of the compounds in FIGS. 4 through 11.

Referring now to FIGS. 4 and 5, two views of the sorbinil molecule demonstrate the immunoregulatory reactive site of the present invention. In FIG. 4, a front view of sorbinil shows the aromatic plane $P_1$ and the plane $P_2$ formed by the center 14 of $P_1$ and the carbonyl oxygen at $X_1$ and the ether oxygen at $X_2$. The distance coordinates $D_1$, $D_2$, and $D_3$ are also indicated. FIG. 5 is an edge view of sorbinil diagrammed so that $X_2$ ($O_1$) is projected toward the viewer. FIG. 5 clearly shows that $P_1$ and $P_2$ are not in the same plane. In FIG. 5, the carbonyl oxygen at $X_1$ is positioned above the plane $P_1$. The angular relationship between the normals to $P_1$ and $P_2$ is $\alpha°=38.85°$ (see TABLE 2). In FIG. 4, a second carbonyl oxygen ($O_{16}$) of sorbinil is much further from the center of $P_1$ ($D_1=5.72$ Å) than is $O_{15}$ ($D_1=4.06$ Å). When sorbinil is viewed on edge in FIG. 5, $O_{16}$ is behind $O_1$ and nearly in the same plane as $P_1$ ($\alpha°=9.89°$); which is much different than the plane $P_1$ that includes $O_{15}$ ($\alpha°=38.85°$). The larger values for $D_1$ and $\alpha°$ exhibited by the $O_{15}$($X_1$) carbonyl are consistent with the three-dimensional conformation necessary for immunoregulatory activity.

Figure 6:
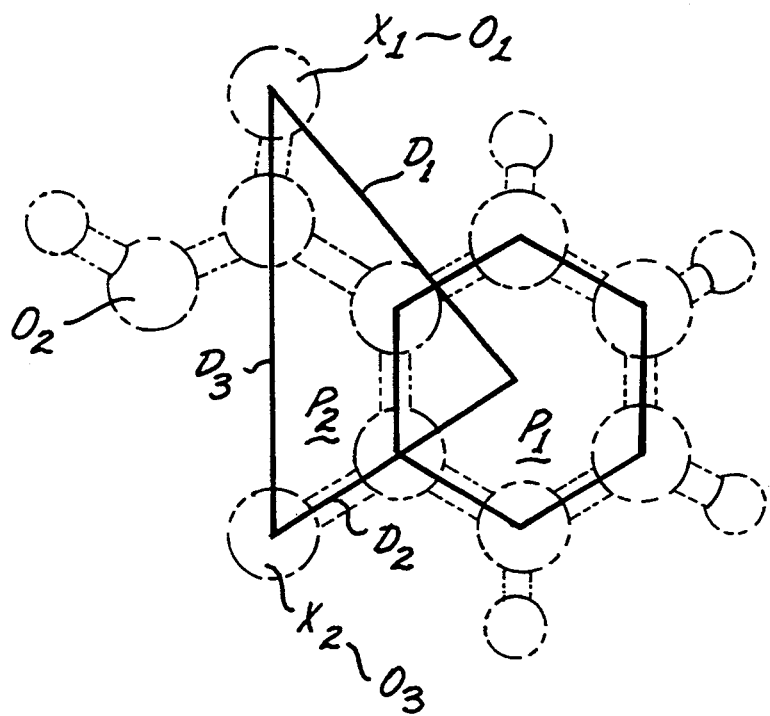
FIG. 6 depicts the immunoregulatory conformation of FIG. 1 superimposed upon the molecular conformation of the deacetylated form of aspirin.
Figure 7:
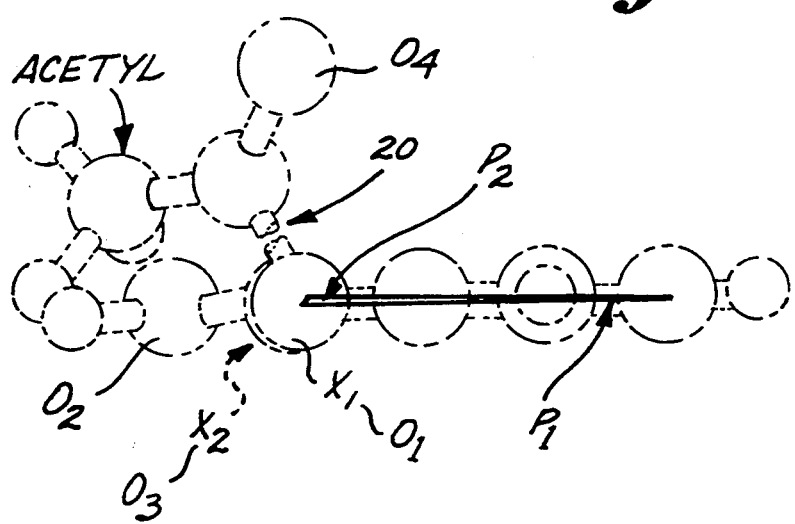
FIG. 7 depicts the immunoregulatory conformation of FIG. 2 superimposed upon the molecular conformation of the deacetylated form of aspirin.

Referring now to FIGS. 6 and 7, the deacetylated form of aspirin is depicted. In contrast to sorbinil, the deacetylated form of aspirin has a low value for $\alpha°$. FIG. 6 is a front view of deacetylated aspirin. The carbonyl oxygen $O_1$, at $X_1$, and the oxygen $O_3$, at $X_2$, form plane $P_2$ with the center 14 of the aromatic plane $P_1$. FIG. 7 demonstrates that planes $P_1$ and $P_2$ are nearly coplanar, $\alpha°=0.69°$; (see TABLE 2). This value for $\alpha°$ is very different than the value $\alpha°=38.85°$ which is present in sorbinil, and this is an important structural basis for the very different activity of the two compounds. FIG. 7 also shows the acetyl group of aspirin that is lost when deacetylation breaks the bond at position 20. Note that the acetylated aspirin has a carbonyl oxygen $0_4$ that occupies a potential $X_1$ position.

Figure 8:
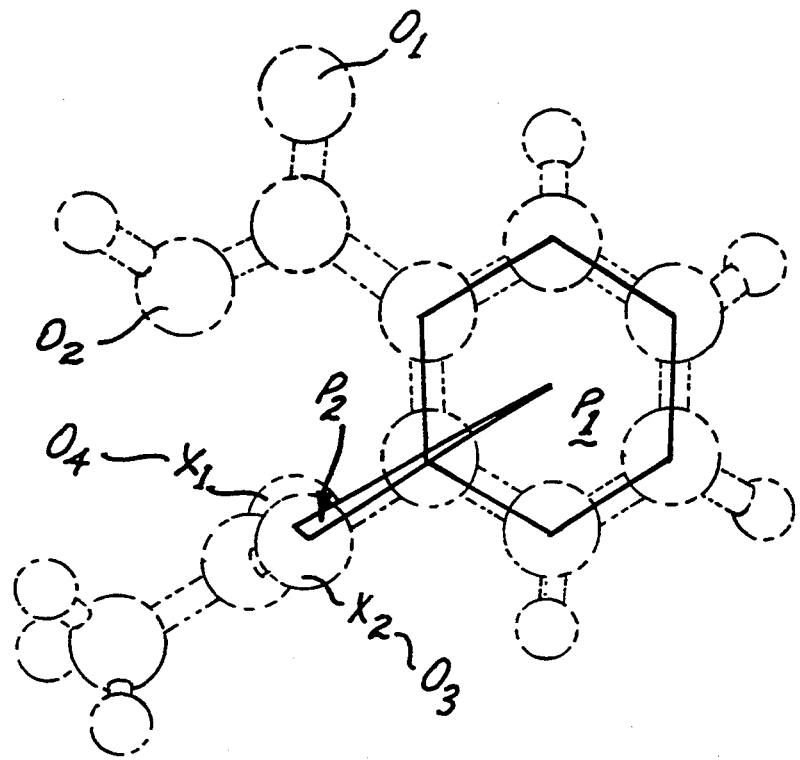
FIG. 8 depicts the immunoregulatory conformation of FIG. 1 superimposed upon the molecular conformation of the acetylated form of aspirin.
Figure 9:
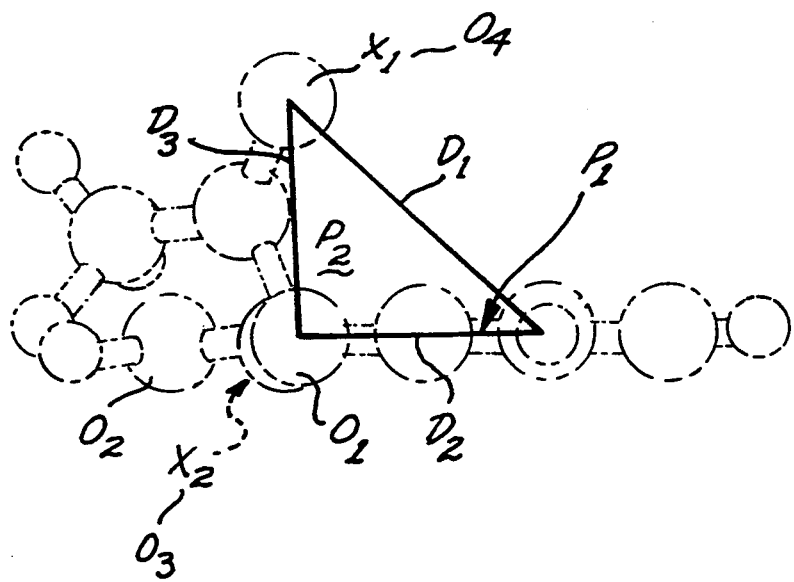
FIG. 9 depicts the immunoregulatory conformation of FIG. 2 superimposed upon the molecular conformation of the acetylated form of aspirin.

FIGS. 8 and 9 show the acetylated form of aspirin. In the acetylated form, $0_4$ is the carbonyl at $X_1$ which forms plane $P_2$ with the center 14 of $P_1$ and the ether oxygen $O_3$ at $X_2$. In the acetylated form, $\alpha°=86.87°$. $P_2$ is nearly orthogonal to plane $P_1$ as shown in FIG. 9. The acetylated form is not normally present in vivo due to the rapid hydrolysis of aspirin to salicylate in the blood. It is interesting to note that the hydantoin and pyran structure of sorbinil stabilizes the oxygens $X_1$, $X_2$ so that the angular relationship between $P_1$ and $P_2$ is maintained as $\alpha°=38.85°$. We contemplate that this stabilizing effect is very significant and is responsible for the immunoregulatory action of sorbinil as compared to the anti-inflammatory action of aspirin.

Figure 10:
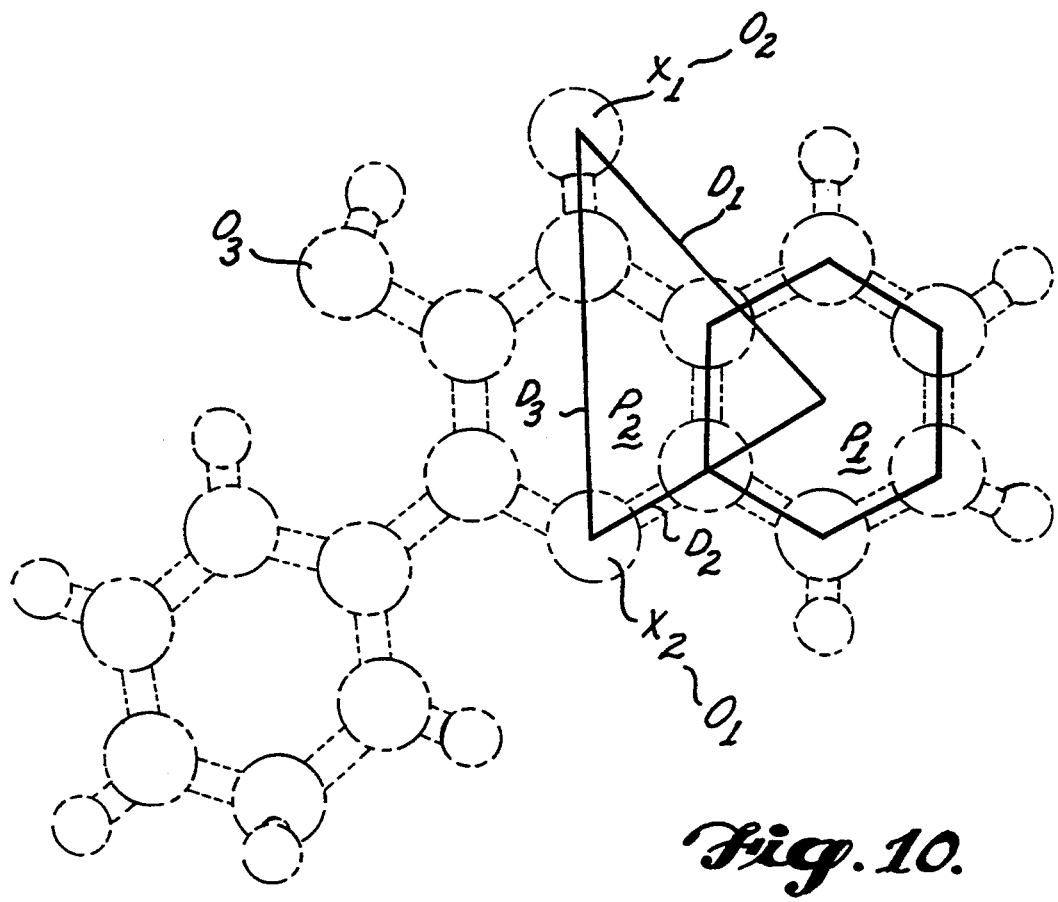
FIG. 10 depicts the immunoregulatory conformation of FIG. 1 superimposed upon the molecular conformation of 3-hydroxyflavone.
Figure 11:
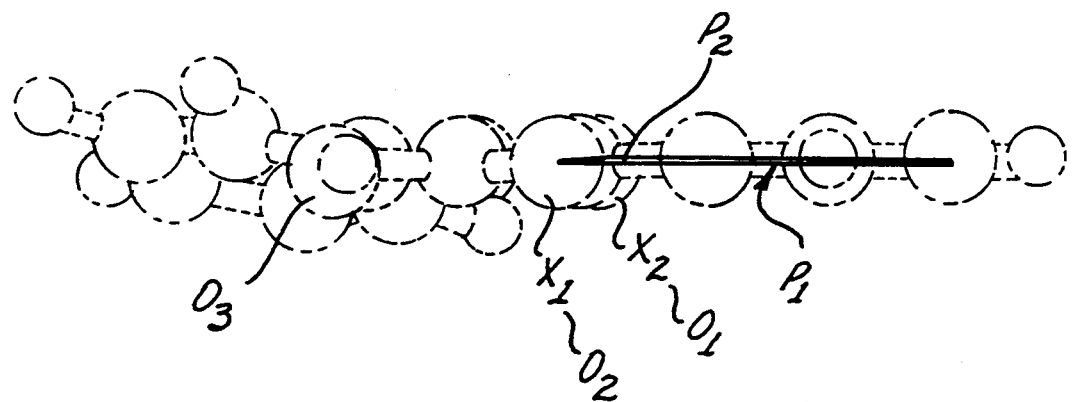
FIG. 11 depicts the immunoregulatory conformation of FIG. 2 superimposed upon the molecular conformation of 3-hydroxyflavone.

FIGS. 10 and 11 show the relationship between the immunoregulatory model and the three-dimensional molecular structure of 3-hydroxyflavone. Planes $P_1$ and $P_2$ of the flavone are very similar to planes $P_1$ and $P_2$ of the deacetylated aspirin. The $\alpha°$ for flavone is 0.69, which is the same value as for deacetylated aspirin and much less than the $\alpha°$ of sorbinil. Again, these different $\alpha°$ values suggest there might be potential differences between the anti-inflammatory activities of sorbinil and the flavones.

Formulas 1 and 2 present the atomic numbering systems from which the coordinates of the reactive conformations for tolrestat and WF-3681 in TABLE 2 are taken. Formula 1 shows tolrestat, as disclosed in Varughese, K. I., et al., Can. J. Chem. 61: 2137–2140, 1983, which is hereby incorporated by reference.

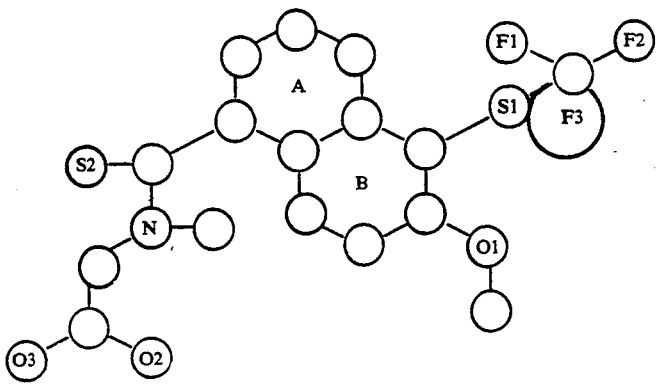

1

Referring to formula 1, aromatic ring 12 in the tolrestat molecule is represented by A, interactive atom $X_1$ by sulfur atom $S_2$, and interactive atom $X_2$ by oxygen atom $O_2$.

Formula 2 shows the molecular structure of WF-3681, as disclosed in Kissinger, C. R., et al., Acta Cryst. C44: 512–514, 1988, which is hereby incorporated by reference.

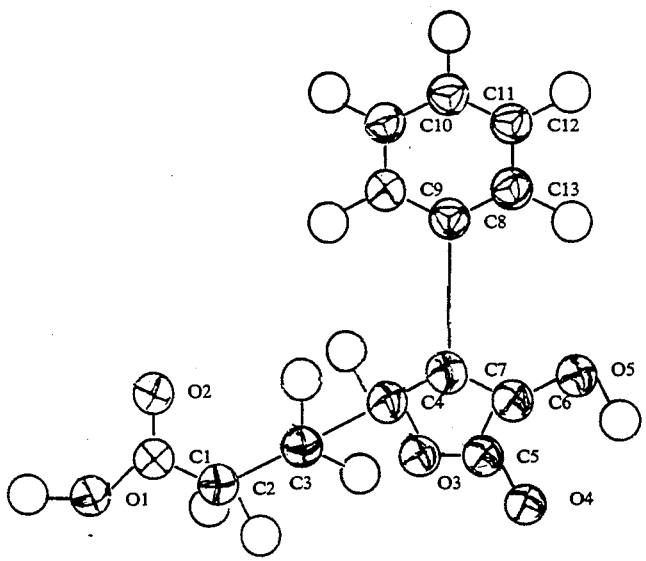

2

Referring to formula 2, aromatic ring 12 in the WF-3681 molecule is represented by C4-O3-C5-C6-C7, interactive atom $X_1$ by oxygen atom $O_2$, and interactive atom $X_2$ by oxygen atom $O_4$.

Based on the foregoing observations, sorbinil, tolrestat, and WF-3681 were tested using the delayed-type hypersensitivity (DTH) assay. Delayed-type hypersensitivity is a general anti-inflammatory reaction, characterized by swelling, redness, heat and pain, that is regulated by cellular components of the immune system. We found that all three compounds produce a strong and substantially identical inhibitory effect on the delayed-type hypersensitivity reaction. Further experiments demonstrated that sorbinil also affects T-cell proliferation and B cell antibody production in unusual and surprising ways. Notably, at least sorbinil and WF-3681 do not alter the normal metabolites of the arachidonic acid pathway in the normal, unstimulated animal. Sorbinil, tolrestat, and WF-3681 are thus representative of a new class of immunoregulatory compounds that, like aspirin and flavones, have anti-inflammatory activity but that unlike aspirin and the flavones affect cellular and humoral components of the immune system.

With regard to anti-convulsant activity, it is interesting to note that the sorbinil structure also includes a hydantoin ring, as in diphenylhydantoin and phenobarbital. We recognized that the hydantoin ring is important to anti-convulsant activity and, based upon this relationship, we predicted that sorbinil exhibits anti-convulsant activity in addition to immunoregulatory activity. The anti-convulsant activity of sorbinil has since been independently reported; see Hall, P. C., and K. L. Keim, Anticonvulsant activity of sorbinil and AL-1576: hydantoin-containing aldose reductase inhibitors, Federation Proceedings 46(3): 433, 606A, 1987.

In sorbinil the pyran ring stabilizes the relationships between $X_1$ and $X_2$, and between the planes $P_1$ and $P_2$. We contemplate that this stability is important to the immunoregulatory activities of sorbinil. We also note that many of the analogs of sorbinil that have been reported to possess aldose reductase activity have molecular configurations that include the above-defined immunoregulatory conformation. Thus, the sorbinil analogs that possess immunoregulatory activity can be defined as the group consisting of those of the formulas:

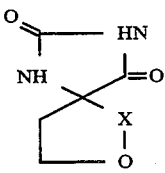

and the base salts thereof with pharmacologically acceptable cations, wherein X is:

benz-$\alpha,\beta$-O or substituted benz-$\alpha,\beta$-O of the formula:

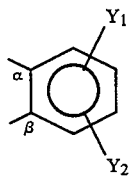

wherein $Y_1$ is hydrogen and $Y_2$ is hydrogen, hydroxy, fluorine, chlorine, lower alkyl or lower alkoxy (each having from one to four carbon atoms);

or $Y_1$ and $Y_2$ when taken separately, are each chlorine, lower alkyl or lower alkoxy, and when taken together are —OCH$_2$(CH$_2$)$_n$O—;

and n is zero or one; (U.S. Pat. Nos. 4,147,795; 4,130,714);

substituted benz-$\alpha,\beta$-O of the formula:

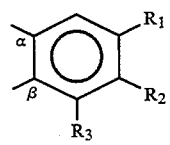

wherein $R_1$ is chlorine, bromine, fluorine, or alkyl of one to three carbon atoms;

one of $R_2$ and $R_3$ is hydrogen;

and the other of $R_2$ and $R_3$ is amino, monoalkylamino or dialkylamino, wherein each alkyl group has from one to three carbon atoms (U.S. Pat. No. 4,248,882);

phenyl or phenoxy substituted benz-$\alpha,\beta$-O of the formula:

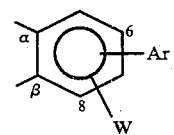

wherein W is hydrogen, methyl, methoxy, phenyl, phenoxy, fluorine, chlorine, or boron at the 6 or 8 position;

and Ar is phenyl or phenoxy at the 6 or 8 position (U.S. Pat. No. 4,181,729);

naph-$\alpha,\beta$-O of the formula:

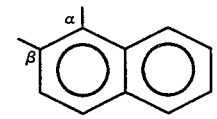

substituted naph-$\alpha,\beta$-O having one or two identical substituents selected from methyl, chlorine, or bromine (U.S. Pat. No. 4,181,728); or anthracene-$\alpha,\beta$-O of the formula:

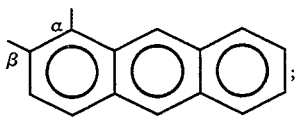

(U.S. Pat. No. 4,181,728).

Sorbinil and its foregoing listed analogs are useful as immunoregulators, and as such are of therapeutic value in the treatment of autoimmune diseases, allergic reactions, hypersensitivity reactions, inflammation, inflammatory dermatitis, undesirable side effects of immunization, graft vs. host rejection, and complications of bone marrow transplant. As used in the claims and specification hereof, treatment is meant to include prevention and/or alleviation of such conditions.

The subject immunoregulatory compounds may be administered to a human patient or other mammalian host in need of treatment by a variety of conventional routes of administration, including orally and parenterally. In general, these compounds will be administered at dosages between 1 and 250 mg per kg body weight of the subject to be treated per day. However, some variation in dosage will necessarily occur depending on the condition of the patient being treated, and the physician will, in any event, determine the appropriate dose for the individual patient.

Pharmaceutically acceptable salts can be readily prepared from sorbinil and sorbinil analogs by conventional methods. Thus, such salts may be prepared by treating the sorbinil or sorbinil analog with an aqueous solution of the desired pharmaceutically acceptable metallic hydroxide or other metallic base and evaporating the resulting solution to dryness, preferably under reduced pressure. Alternatively, a lower alkanoic solution of the sorbinil or sorbinil analog may be mixed with an alkoxide of the desired metal, and the solution subsequently evaporated to dryness. The pharmaceutically acceptable hydroxides, bases, and alkoxides include those with cations that form metal salts with the acidic compounds of sorbinil and its analogs and that are nontoxic at the dosages administered to a patient in need of treatment. Suitable cations for this purpose include, but are not limited to, potassium, sodium, ammonium, calcium, and magnesium.

The compounds may be administered alone or in combination with pharmaceutically acceptable carriers, in either single or multiple doses. Suitable pharmaceutical carriers include inert solid diluents or fillers, sterile aqueous solutions and various nontoxic organic solvents. The pharmaceutical compositions formed by combining the sorbinil or sorbinil analog with the pharmaceutically acceptable carrier are then readily administered in a variety of dosage forms, such as tablets, powders, lozenges, syrups, injectable solutions and the like. These pharmaceutical compositions can, if desired, contain additional ingredients such as flavorings, binders, excipients, and the like. Thus, for purposes of oral administration, tablets containing various excipients such as sodium citrate, calcium carbonate, and calcium phosphate may be employed along with various disintegrants such as starch, and preferably potato or tapioca starch, alginic acid, and certain complex silicates, together with binding agents such as polyvinylpyrrolidine, sucrose, gelatin, and acacia. Additionally, lubricating agents, such as magnesium stearate, sodium lauryl sulfate, and talc are often useful for tableting purposes. Solid compositions of a similar type may also be employed as fillers in salt and hard-filled gelatin capsules; preferred materials for this purpose include lactose or milk sugar and high molecular weight polyethylene glycols. When aqueous suspensions of elixirs are desired for oral administration, the essential active ingredient therein may be combined with various sweetening or flavoring agents, colored matter or dyes, and, if desired, emulsifying or suspending agents, together with diluents such as water, ethanol, propylene glycol, glycerin, and combinations thereof. For parenteral administration, solutions of the sorbinil or sorbinil analog in sesame or peanut oil or in aqueous propylene glycol may be employed, as well as sterile aqueous solutions of the corresponding water soluble pharmaceutically acceptable metal salts previously described. Such an aqueous solution should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well known to those skilled in the art. Additionally, it is also possible to administer the aforesaid compounds topically via an appropriate solution suitable for the present purposes at hand.

The subject compounds, when formulated as described above, will typically be packaged with printed instructions specifying their use for regulating the immune system, e.g., by inhibiting the delayed type hypersensitivity reaction.

In order to assist in a better understanding of the present invention, the results of various experiments are set forth below.

Experiment 1

The crystal and molecular structure of sorbinil was determined using 3-D X-ray diffraction methods as disclosed in Kissinger, C. R., et al., Acta Cryst. C41: 988–990, 1985, which is hereby incorporated by reference.

Sample of sorbinil provided by Pfizer Inc. (Lot No. 11,396-235-1B). Crystallized by slow evaporation from acetone and water solution. Crystal dimensions, $0.85 \times 0.65 \times 0.40$ mm. KRISEL Control-updated Picker FACS-1 diffractometer. $CuK\alpha$ radiation. Cell constants determined by least-squares from 16 reflections ($22° < 2\theta > 47°$). $\omega$-$2\theta$ scans, $2°$ min$^{-1}$. Absorption correction applied (1.02 to 1.07). Maximum (sin $\theta$)/$\lambda = 0.5305$ (h 0-7, k 0-6, l 0-22), 5 standard reflections showed no significant variation. 792 reflections, 762 unique, 19 unobserved (F < 4 $\sigma_F$). Lorentz-polarization corrections applied. No deterioration correction. Structure solved by direct methods using RANTAN80 (Yao, 1981). Full matrix least-squares refinement on F. Anisotropic temperature factors for non-hydrogen atoms, isotropic temperature factors for hydrogen atoms. H atoms located in a difference map. R = 0.042, R$_w$ = 0.048 (w = 1/$\sigma_F$), mean and max. $\Delta/\sigma$ 0.0799 and 0.9672. Isotropic extinction parameter refined to a value of 0.0124(3). Scattering factors for C, N and O from Cromer, D. T., et al., Acta Cryst. A24: 321–24, 1968. Scattering factors for H from Stewart, R. F., et al., J. Chem. Phys. 42: 3175–87, 1965. Scattering factors for F from International Tables for X-ray Crystallography (1974). Refinement using programs from XRAY76; Stewart, J. M., et al., Tech. Rep. TR-446, Computer Science Center, University of Maryland, College Park, Md. 1976.

Figure 12:
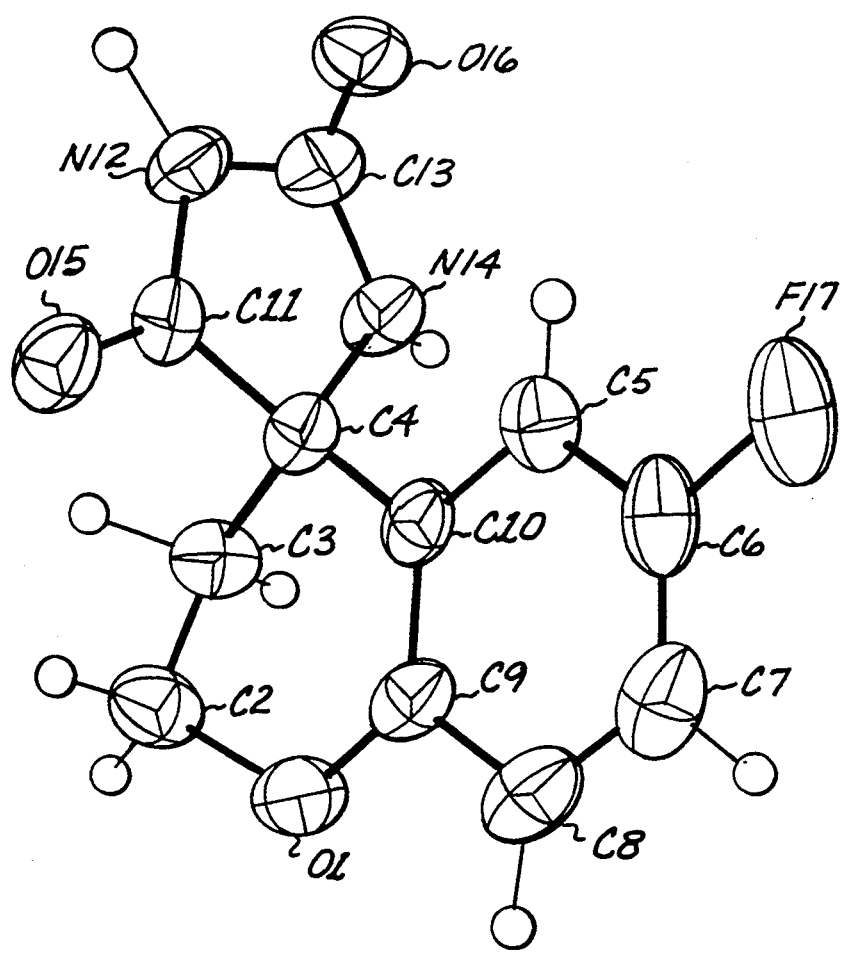
FIG. 12 depicts the precise three-dimensional conformation of sorbinil, as described in Experiment 1 herein.

The three-dimensional conformation of sorbinil is depicted in FIG. 12. The bond lengths and bond angles are listed in TABLES 3 and 4.

TABLE 3

| Bond Lengths (Å) for sorbinil. | | | |
|---|---|---|---|
| O(1)–C(2) | 1.450 | C(9)–C(10) | 1.378 |
| C(2)–C(3) | 1.484 | C(9)–O(1) | 1.374 |
| C(3)–C(4) | 1.540 | C(4)–C(11) | 1.537 |
| C(4)–C(10) | 1.516 | C(11)–O(15) | 1.217 |
| C(10)–C(5) | 1.403 | C(11)–N(12) | 1.364 |
| C(5)–C(6) | 1.370 | N(12)–C(13) | 1.410 |
| C(6)–F(17) | 1.386 | C(13)–O(16) | 1.225 |
| C(6)–C(7) | 1.362 | C(13)–N(14) | 1.345 |
| C(7)–C(8) | 1.374 | N(14)–C(4) | 1.458 |
| C(8)–C(9) | 1.398 | | |

TABLE 4

| Bond angles ($\alpha°$) for sorbinil. | | | |
|---|---|---|---|
| O(1)–C(2)–C(3) | 110.3 | C(1)–C(9)–C(8) | 115.3 |
| C(2)–C(3)–C(4) | 110.6 | C(3)–C(4)–N(14) | 111.7 |
| C(3)–C(4)–C(10) | 110.1 | C(3)–C(4)–C(11) | 110.0 |
| C(4)–C(10)–C(9) | 121.2 | C(10)–C(4)–N(14) | 112.7 |
| C(10)–C(9)–O(1) | 123.4 | C(10)–C(4)–C(11) | 111.9 |
| C(9)–O(1)–C(2) | 114.5 | C(4)–C(11)–N(12) | 107.8 |
| C(10)–C(5)–C(6) | 117.7 | C(11)–N(12)–C(13) | 111.1 |
| C(5)–C(6)–C(7) | 124.1 | C(12)–N(13)–C(14) | 107.2 |
| C(6)–C(7)–C(8) | 118.5 | C(13)–N(14)–C(4) | 113.6 |
| C(7)–C(8)–C(9) | 119.4 | N(14)–C(4)–C(11) | 100.2 |
| C(8)–C(9)–C(10) | 121.3 | C(4)–C(11)–O(15) | 125.8 |
| C(9)–C(10)–C(5) | 119.1 | N(12)–C(11)–O(15) | 126.4 |
| C(4)–C(10)–C(5) | 119.7 | N(12)–C(13)–O(16) | 125.5 |
| C(5)–C(6)–F(17) | 117.1 | N(14)–C(13)–O(16) | 127.3 |
| C(7)–C(6)–F(17) | 118.9 | | |

The immunoregulatory effects of sorbinil were discovered and documented in the following series of immunological experiments.

First Series of Immunological Experiments

The ability of sorbinil to inhibit the immunologically mediated inflammation which occurs during delayed type hypersensitivity (DTH) was tested in the following series of experiments. Delayed type hypersensitivity, which involves the participation of T lymphocytes and macrophages, can be studied in vivo by exposing (or priming) a mammal to a novel antigen and then reexposing (or challenging) the primed animal to the same antigen four to seven days later. The classic DTH response includes symptoms of inflammatory response, induration and erythema, which peak at 24 to 48 hours after challenging and then decline slowly.

Experiment 2

Eight-week old female C57BL/6J mice (Jackson Labs) were divided into primed and unprimed groups. The five mice in the primed group were primed to 2,4-dinitrofluorobenzene (DNFB; Sigma Chemical Co., Grade 1, approx. 98%, Lot 129C-0065, No. d-6879) by painting their shaved ventral skins with 0.1 ml of 0.5% DNFB in ethanol:acetone (3:1). The five mice in the unprimed group were shaved and topically painted on their ventral skins with the ethanol:acetone (3:1) vehicle alone. The mice in both groups were challenged with DNFB four days later. A suitable patch of skin, the ear, was chosen for challenging. One ear was designated for challenging and the other to serve as a control. The thickness of each ear across the pinna was measured using micrometer calipers. The first measurements were taken four days after priming and are plotted as day 0 in FIG. 13. Next, each mouse was subjected to the following challenge regimen: one ear was challenged with one drop of 0.35% DNFB in olive oil, and the other (unchallenged control) ear was exposed to olive oil alone. The ear thicknesses (ET) of the challenged ear and the unchallenged ear were measured daily, and the swelling responses are plotted in FIG. 13 as:

$$\text{Swelling \%} = \frac{ET \text{ challenged ear} - ET \text{ unchallenged ear}}{ET \text{ unchallenged ear}} \times 100\%$$

Figure 13:
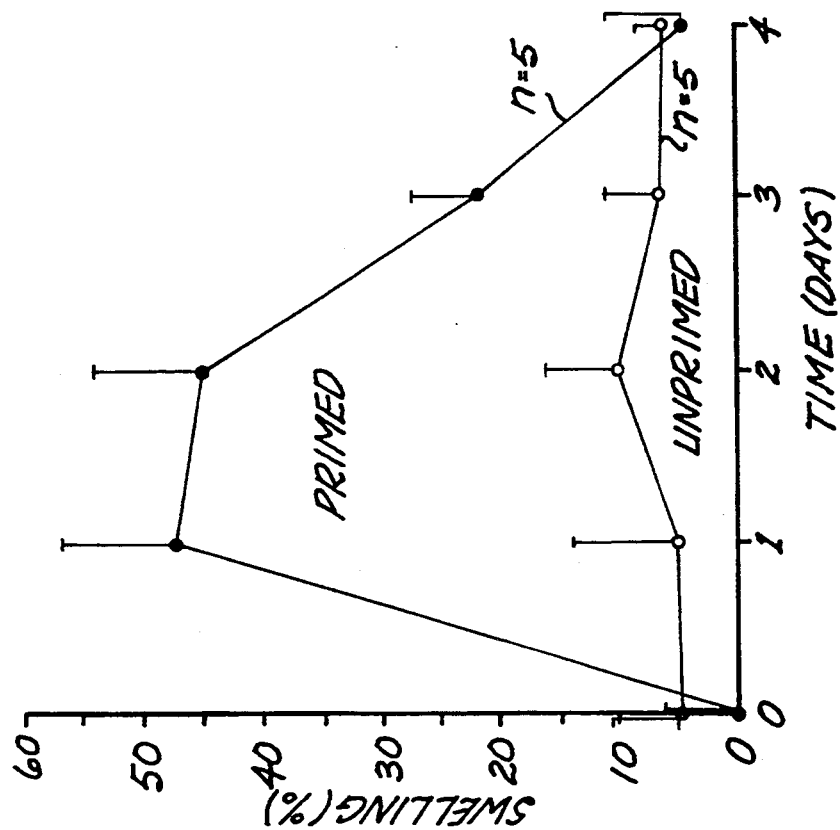
FIG. 13 is a graph which summarizes the results of Experiment 2 as described herein.

Referring now to FIG. 13, animals previously exposed to DNFB (primed) showed a much greater response to the ear challenge than did animals that had not been previously exposed to DNFB (unprimed). Maximum swelling was observed one day after challenging. Swelling (%) was nine times greater in the primed animals than in unprimed animals. Erythema was also noted in the challenged ears of the primed animals.

This experiment demonstrated that these mice would develop an inflammatory response to this novel antigen, and the primed and unprimed curves in FIG. 13 served as controls with which any anti-inflammatory effect of sorbinil could be compared.

Experiment 3

An experiment to test the anti-inflammatory activity of sorbinil was run concurrently with Experiment 2. Three groups of eight-week old female C57BL/6J mice were primed to DNFB as previously described. Four days later, these primed groups received sorbinil (MW=236.12; Pfizer Lot No. 11,396-235-1B) orally at concentrations of 10, 1.0, or 0.1 mg/kg body weight per mouse. Six hours later the first sets of ear measurements were taken, and one ear of each mouse was challenged. Sorbinil was subsequently administered at the stated concentrations six hours before each daily measurement of ear thicknesses. Swelling responses were calculated as previously described, and the data are presented in FIG. 14.

Figure 14:
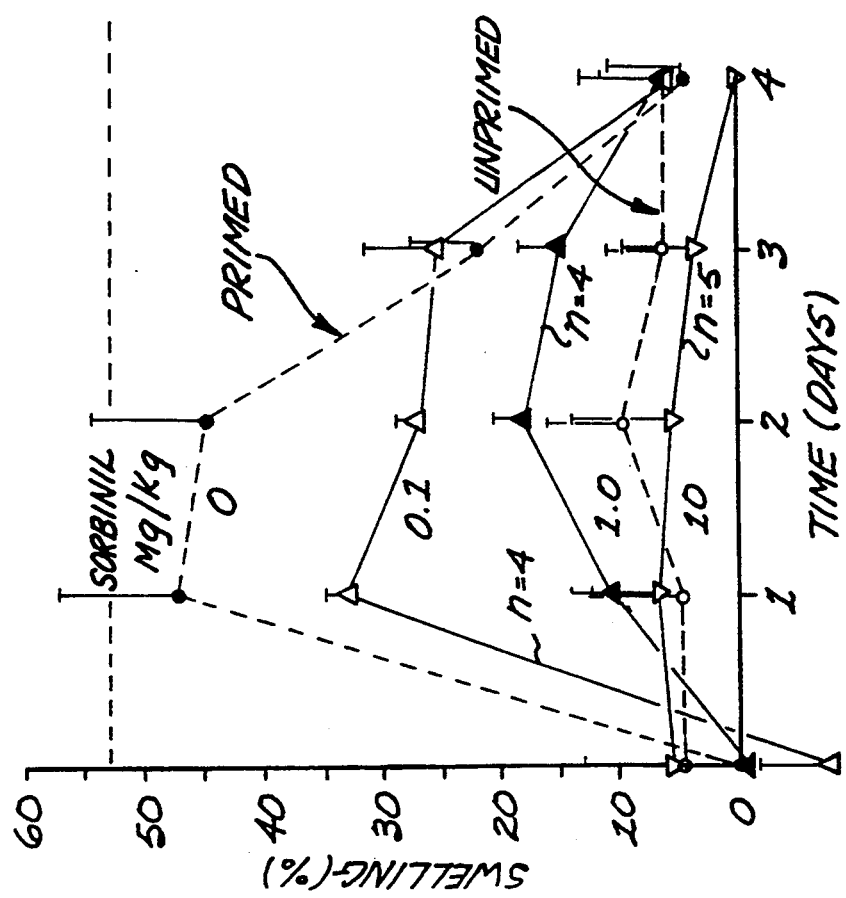
FIG. 14 is a graph which summarizes the results of Experiment 3 and shows that sorbinil inhibits the inflammatory response associated with the delayed-type hypersensitivity reaction.

Referring now to FIG. 14, the primed and unprimed curves from FIG. 13 are reproduced as dotted lines, and the inflammatory responses of the three sorbinil-treated groups are plotted as solid lines. Swelling was inhibited in animals that received sorbinil. Moreover, there was a dose dependent inhibition of ear swelling: the sorbinil was more effective at inhibiting ear swelling at higher concentrations. Sorbinil at a concentration of 10 mg/kg resulted in almost complete inhibition of ear swelling, as evidenced by the general confluence of the 10 mg/kg curve with that of the unprimed curve.

Figure 15:
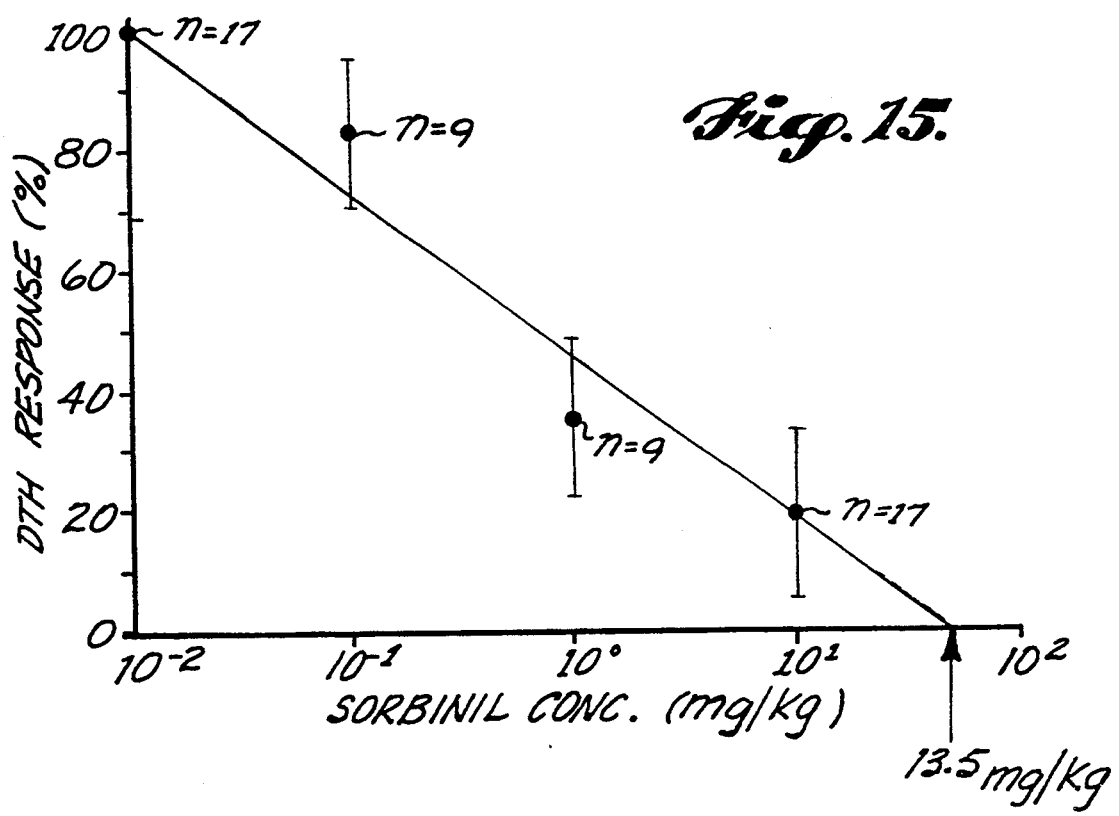
FIG. 15 is a graph which shows that sorbinil causes a dose dependent inhibition of the delayed-type hypersensitivity response.

Referring now to FIG. 15, the dose effect of sorbinil is characterized by presenting the data accumulated from three replicates of Experiment 3. DTH response (%) is plotted versus sorbinil concentration (mg/kg) on a semilogarithmic scale, where $$DTH \text{ response (\%)} = \frac{\text{Ear swelling (\%) in mice given drug}}{\text{Ear swelling (\%) in vehicle control mice}}$$

The data in FIG. 15 is derived from three experiments using C57BL/6J mice. The measurements were taken at the time of maximal swelling, i.e., 2 hours after challenge, and each point represents at least 9 mice. The data show that inhibition of the inflammatory response is dose dependent and may vary linearly with the log of the sorbinil dosage. Extrapolations from a least squares fit line indicates that maximum inhibition of DTH response (no swelling) would occur at a concentration of 13.5 mg sorbinil/kg body weight. Sorbinil significantly inhibits the DTH response, and thus it may have potential as a new anti-inflammatory agent for therapeutic uses that include the control of contact dermatitis and allograft rejection.

Experiment 4

Experiments 2 and 3 were repeated with Balb C NCI mice (Life Sciences, Inc., St. Petersburgh, Fla.). A similar dosage dependent mediation of the classic DTH response was observed in the mice that received sorbinil.

Experiment 5

Histologic examination of ear tissue from sorbinil-treated and challenged control mice indicated that mononuclear cell infiltration occurred in the challenged ears of both groups, although infiltration was reduced in the group treated with sorbinil.

Figure 16:
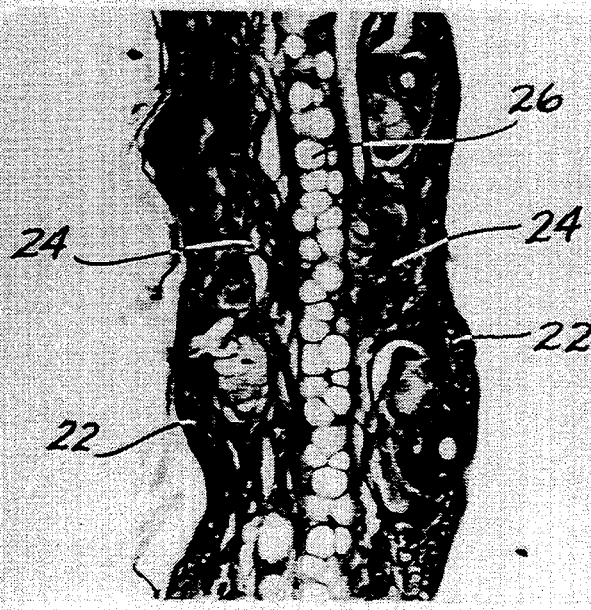
FIG. 16 is a photomicrograph (approximately 700 X) of a cross section of the pinna of a normal primed mouse that was not challenged with DNFB, as described in Experiment 5 herein.
Figure 17:
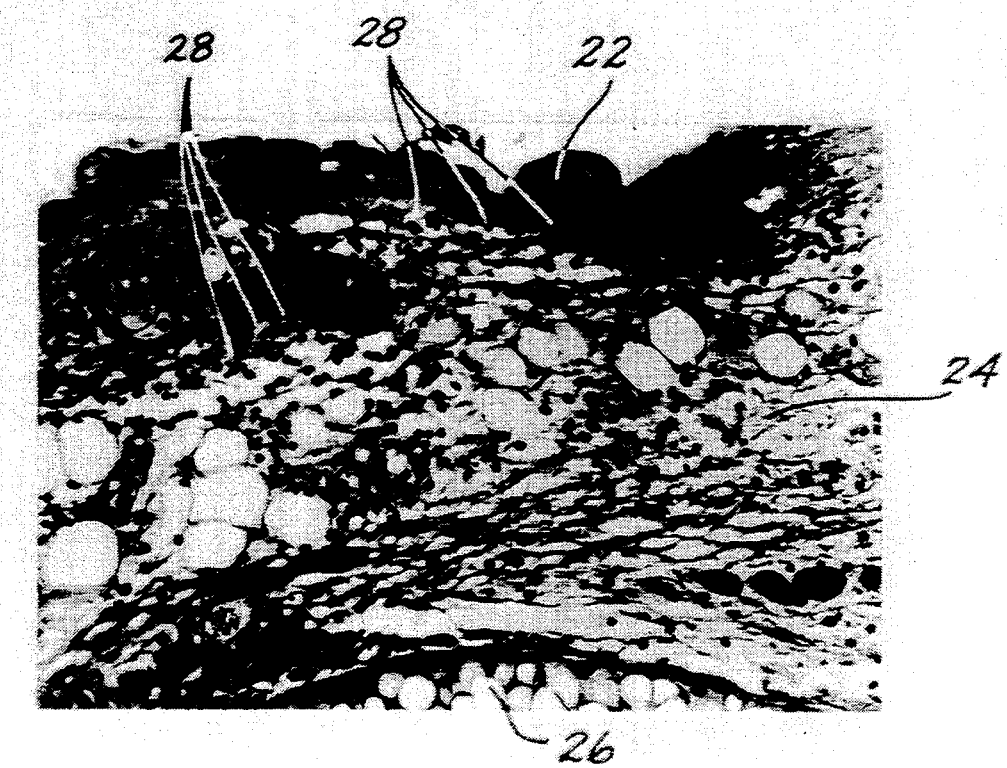
FIG. 17 is a photomicrograph as in FIG. 16 but of a buffer-treated control mouse that was challenged with DNFB.
Figure 18:
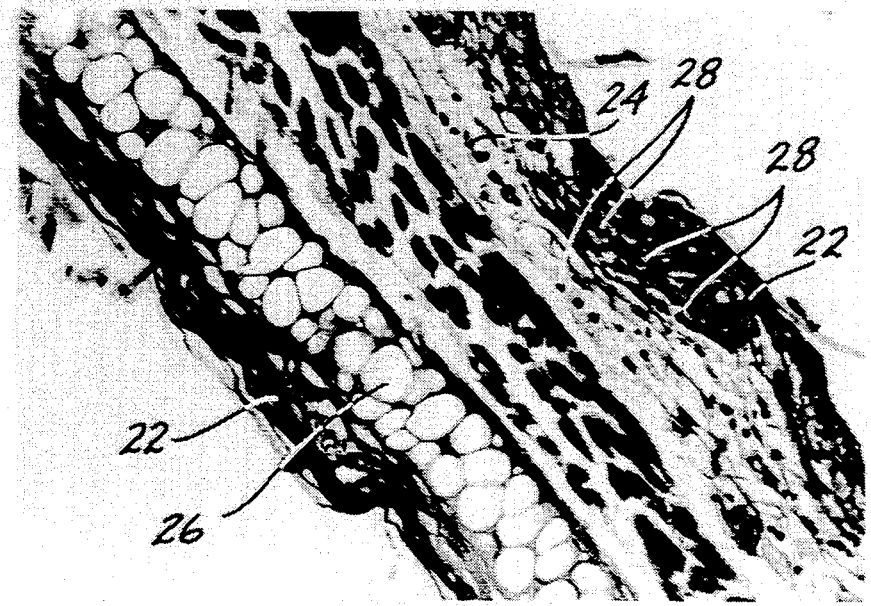
FIG. 18 is a photomicrograph as in FIG. 16 but of a sorbinil-treated primed mouse that was challenged with DNFB.
Figure 19:
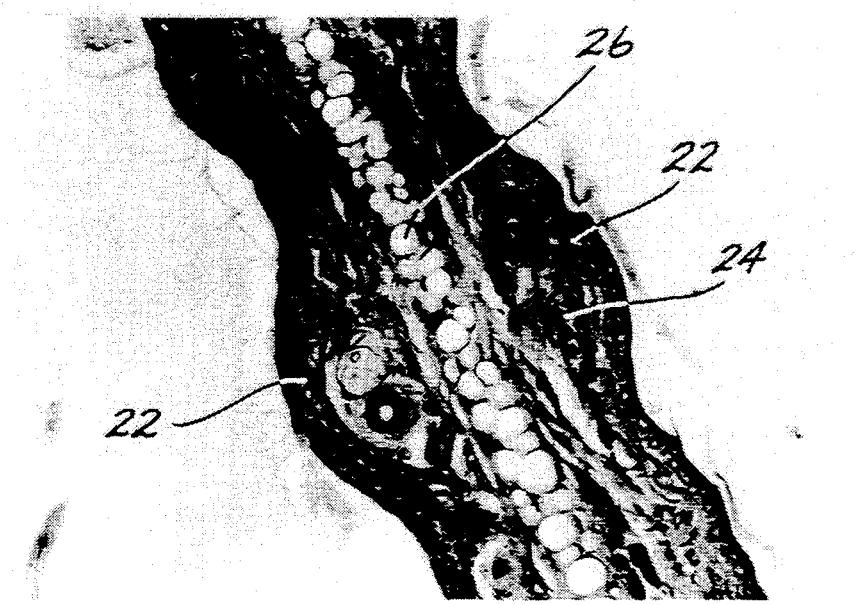
FIG. 19 is a photomicrograph as in FIG. 16 but of a primed mouse treated with sorbinil but not challenged with DNFB.

Referring now to FIGS. 16, 17, 18, and 19, the histologic features of the DTH reaction in ears from mice treated with buffer (FIGS. 16 and 17) or sorbinil (FIGS. 18 and 19) are shown. FIG. 16 depicts the ear of a primed mouse which has not been challenged with DNFB. The epidermis 22 is devoid of mononuclear infiltrate 28, as is the dermal compartment 24. A layer of cartilage 26 is located in the center of the ear. FIG. 17 represents the ear of a buffer-treated primed mouse which had been challenged 24 hours previously with DNFB. Note the pronounced edema in the dermal compartment of the skin 24 as well as the extensive mononuclear cell infiltrate (indicated by arrows 28) in both the dermis and epidermis. The histologic appearance of the sorbinil-treated primed mouse challenged 24 hours previously with DNFB is shown in FIG. 18. In marked contrast to the histologic appearance of the buffer-treated primed mice, the dermal compartment 24 is much less edematous and contained fewer mononuclear cells 28. There were also fewer mononuclear cells 28 in the epidermis 22 as well. In FIG. 19, the ear of a primed mouse treated with sorbinil but not challenged with DNFB is shown. As with the buffer-treated primed mice, the unchallenged ear is devoid of edema and does not contain infiltrating mononuclear cells.

The histologic section in FIG. 18 indicates that the inhibition of swelling by sorbinil is accompanied by a mild cellular infiltration. This mild response suggested that sorbinil may affect not only the secretion of inflammatory mediators, but also the recruitment of cells to the site of inflammation. To our knowledge this type of immunoregulation has never been observed.

Discussion

The results of this first series of experiments were intriguing. In Experiment 2, the development of the DTH type of cell-mediated immunity was demonstrated in the murine model. Experiments 3 and 4 demonstrated that sorbinil causes a dose dependent inhibition of that DTH response. Yet Experiment 5 suggested that sorbinil does not cause a total inhibition of that immune response: the presence of infiltrating mononuclear cells in the challenged ears of the sorbinil-treated mice suggested that antigen recognition had occurred but that the effector mechanism of inflammation was specifically inhibited by the sorbinil. It is generally accepted that the delayed type hypersensitivity reaction involves the participation of specifically sensitized T-lymphocytes and macrophages. The macrophages appear to function in two capacities: (1) as accessory cells that present the novel antigen to and thereby specifically sensitize the T-lymphocytes (antigen recognition), and then (2) as effector cells in DTH reactions after responding to mediators produced by the sensitized T-lymphocytes. These two functions may be correlated with the heterogeneity of the macrophage population: Some macrophages (or macrophage progenitors) are excellent antigen presenting cells, while other populations of macrophages are more active as effector cells.

Additional experiments were therefore devised to determine how sorbinil inhibits the DTH response. It is known that if the requirement of antigen presentation by macrophages is met, then T-cells can be sensitized to the antigen and activated. Activated T-cells proliferate and express IL-2 receptors, and some activated T-cells secrete IL-2. Activated T-cells also secrete other mediators, e.g., macrophage inhibition factor (MIF), interferons, and other soluble factors. Some of these T-cell products, e.g., MIF and $\alpha,\beta$ interferons, can activate macrophages. The activated macrophages in turn secrete IL-1 (endogenous pyrogen), catabolic enzymes (e.g., collagenase, hylaronidase, neutral proteinase), and prostaglandins of the E-series. Thus, macrophages are not only necessary for antigen presentation to T-cells but are also the effector cells that cause the symptoms of immunologically mediated inflammation by secreting IL-1, prostaglandins, and catabolic enzymes at the challenged site.

The immune system involves a complex series of cellular interactions which regulate the production of lymphocytes and mononuclear phagocytes, as well as affecting their differentiated function. The interdependence of these different cell populations in the immune system is reflected by their obligatory interactions for effective function. Most T-cell function is dependent on the participation of macrophages for antigen presentation. Also, B cells require helper T-cells in order to produce antibodies to most antigens; the helper T-cells in turn require the participation of macrophages or accessory cells for antigen presentation. Interactions between T lymphocytes and macrophages thus play a central role in the immune system by affecting: T lymphocyte activation and proliferation, generation of T helper activity and B lymphocyte antibody response, generation of cytotoxic T lymphocyte response, and macrophage activation. Additional experiments were designed to determine if sorbinil affects these other parameters of the immunological status of mammals. The next two series of experiments examined the effects of sorbinil on B cell antibody production and on T-cell mitogen responsiveness.

Second Series of Immunological Experiments

The effects of sorbinil on B cell antibody production were investigated.

Experiment 6

The effects of sorbinil on primary responses to sheep red blood cells (SRBC) were noted using the direct plaque forming cell (PFC) assay. In this experiment C57BL/6J mice received 11 mg/kg sorbinil orally on a daily basis. A control group received only the buffer vehicle (carbonate buffer, 0.01M, pH 9.5). Six hours after the first dose, the mice received 0.1 ml of a 20% SRBC solution intraperitoneally. The mice were sacrificed four days later. The spleens were harvested, and the spleen cells were tested in a modified Cunningham plaque assay. Cunningham, A. V., Nature (London) 207:1106 1965. The results are summarized as follows:

A 46% increase in cellularity was observed in the spleens of sorbinil-treated mice compared to the buffer-treated control group: $2.12\pm0.26\times10^8$ cells/spleen in the sorbinil group; $1.45\pm0.3\times10^8$ cells/spleen in the control group.

Sorbinil-treated mice exhibited a 94% increase in the number of direct plaques, which are indicative of the number of IgM antibody secreting cells, when compared to the buffer control group: $372\pm62$ plaques per $2\times10^5$ cells in the sorbinil group; $191\pm50$ plaques per $2\times10^5$ cells in the control group. Taking the differences in spleen cellularity into account, and expressing PFC data on a per spleen basis, the differences between sorbinil-treated and control mice were: sorbinil-treated = $393,000\pm12,617$ PFC/spleen; buffer control group = $167,009\pm43,695$ PFC/spleen.

There were also qualitative differences in the plaques. The plaques produced by spleen cells from the buffer-treated control mice were large, rounded, and exhibited the expected clear and distinct zone of SRBC lysis. In contrast, the plaques produced by spleen cells from the sorbinil-treated mice were much smaller, more irregularly shaped, and less distinct. The most likely explanation for this observation is that the rate of antibody secretion by the sorbinil-treated spleen cells was less than that by the spleen cells from the control animals.

Experiment 7

This experiment assessed the effects of sorbinil on antibody production following intravenous immunization of mice with the bacteriophage $\Phi X$ 174. Antibodies generated against the bacteriophage were quantitated by a phage inhibition assay, which is based on the observation that antibodies specific for the bacteriophage will inhibit the ability of the bacteriophage to lyse bacteria. Ochs, H. D., et al., Disorders of the B-cell system, in Immunologic Disorders in Infants and Children, E. R. Stiehm, et al., eds., W. B. Sanders, Co. Philadelphia, p. 239, 1980. The data was expressed as Kv values derived according to the following formula: Rate of phage inactivation, Kv $D/T\times \ln Po/P$, where D = reciprocal of antibody dilution, T = 60 minutes, Po = initial number of PFU, and P = number of plaques at 60 minutes.

Mice were treated daily for five days with sorbinil using the same dosage schedule as described in Experiment 6. Six hours after administration of the first dose of sorbinil, the mice were injected intravenously with $2\times10^9$ plaque forming units (PFU) of phage. Beginning with one week after this primary immunization mice were bled weekly, and serum samples from individual mice were tested for the ability to inhibit bacteriophage lysis of bacteria. The data from the first two weeks after the primary immunization are summarized as follows:

One week after priming, the serum titers of anti- $\Phi X$ 174 bacteriophage antibodies did not differ significantly: $Kv=5.0\pm2.4$ in the sorbinil-treated group; $Kv=8.3\pm3.1$ in the control group.

By two weeks after primary immunization, serum titers of anti- $\Phi X$ 174 bacteriophage antibodies from sorbinil-treated animals were significantly less than those obtained from control mice which had received only buffer: $Kv=18.4\pm11.4$ in the sorbinil-treated group; $Kv=7.8\pm5.2$ in the buffer-treated group.

Discussion

These results suggest that sorbinil effects the production of antibody in response to antigenic challenge. At first glance, the effects of sorbinil demonstrated in Experiments 6 and 7 appear to be somewhat contradictory: increased splenic cellularity and increased plaque forming responses following immunization, yet serum titers of antibody appear to be reduced. An explanation consistent with these data is that sorbinil affects the antigen-driven maturation of B lymphocytes into plasma cells. In this model, antigen-specific B lymphocytes in sorbinil-treated mice are stimulated to proliferate as they would in normal immunized mice, but in sorbinil-treated mice the proliferating B lymphocytes are prevented from differentiating further into terminally differentiated, nonreplicating plasma cells. Such a blockage in B cell maturation is suggested by the increased cellularity of the spleen and by the increased frequency of antibody-secreting cells in the mice that received sorbinil. Moreover, the observations that the plaques formed by B lymphocytes from sorbinil-treated mice are much smaller and less distinct than those produced by control spleen cells indicates that the B lymphocytes from sorbinil-treated mice are secreting antibodies at a lower rate. This observation also conforms to the model because the terminally differentiated plasma cells have the highest rate of antibody secretion. Furthermore, an inhibition of terminal B lymphocyte maturation which prevented the generation of plasma cells would likely result in reductions of serum antibody levels consistent with those observed in Experiment 7.

It is further contemplated that sorbinil might inhibit the secretion of a soluble mediator of B lymphocyte maturation. The existence of two distinct types of soluble mediators that affect B lymphocyte maturation have been reported, one as affecting proliferation and the other as stimulating B lymphocyte maturation into plasma cells. Howard et al. have described a B cell growth factor found in induced supernatants of the mouse thymoma EL-4. Howard, M., et al., J. Exp. Wed. 155: 914, 1982. This factor is co-stimulating with anti-IgM antibodies in cultures of purified B cell cultures. This factor appears to stimulate B cell proliferation but not production of antibody forming cells. This factor is distinct from another soluble mediator described by Sidman et al. which promotes immature B cell maturation into cells resembling highly differentiated B cells secreting antibody at a high rate; J. Immunol. 132: 209, 1984.

Third Series of Immunological Experiments

In order to further define the immunoregulatory effect of sorbinil, the effect of sorbinil on spleen cell response to the T lymphocyte mitogen Concanavalin A (Con A) was assessed. The proliferative response of T lymphocytes to the Con A mitogen requires the obligatory participation of adherent accessory cells, which are presumed to be macrophages.

Experiment 8

Mice received sorbinil orally for one, two, or three days prior to sacrifice. The dosage was 11 mg/kg per day. Control mice received the buffer vehicle alone. Mice from these four groups were sacrificed and their spleens harvested. The spleens were teased into single-cell suspensions that were cultured with different concentrations of Con A for three or four days. One microcurie of tritiated thymidine was added to each culture 18 hours before the cultures were terminated. Incorporation of the tritiated thymidine into cellular DNA was measured by using a liquid scintillation counter. The results of this experiment are presented in FIGS. 20 and 21 and are summarized as follows:

The kinetics of the proliferative response of spleen cells to Con A was not affected by treatment of the animals with sorbinil for one, two, or three days prior to spleen cell harvesting. The response was greater in cultures harvested on day three (FIG. 20), and a significant drop in proliferative activity was noted in cultures harvested on day four (FIG. 21).

Figure 20:
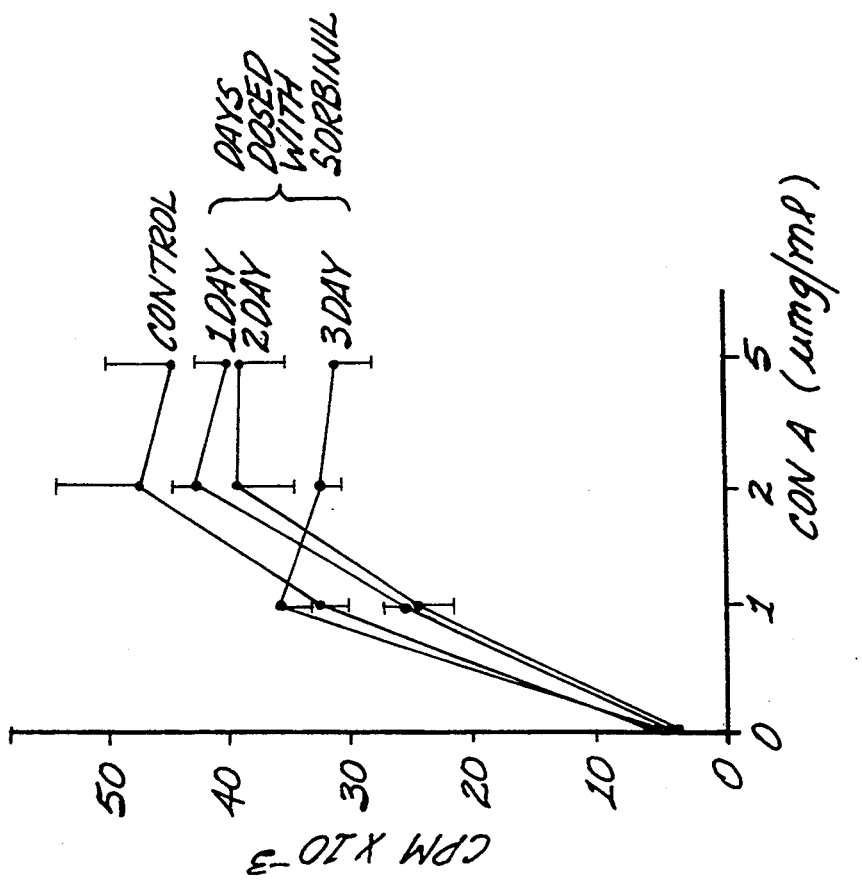
FIG. 20 is a graph which shows that sorbinil inhibits the proliferative response of T-cells to the mitogen Con A, as described in Experiment 8 herein.
Figure 21:
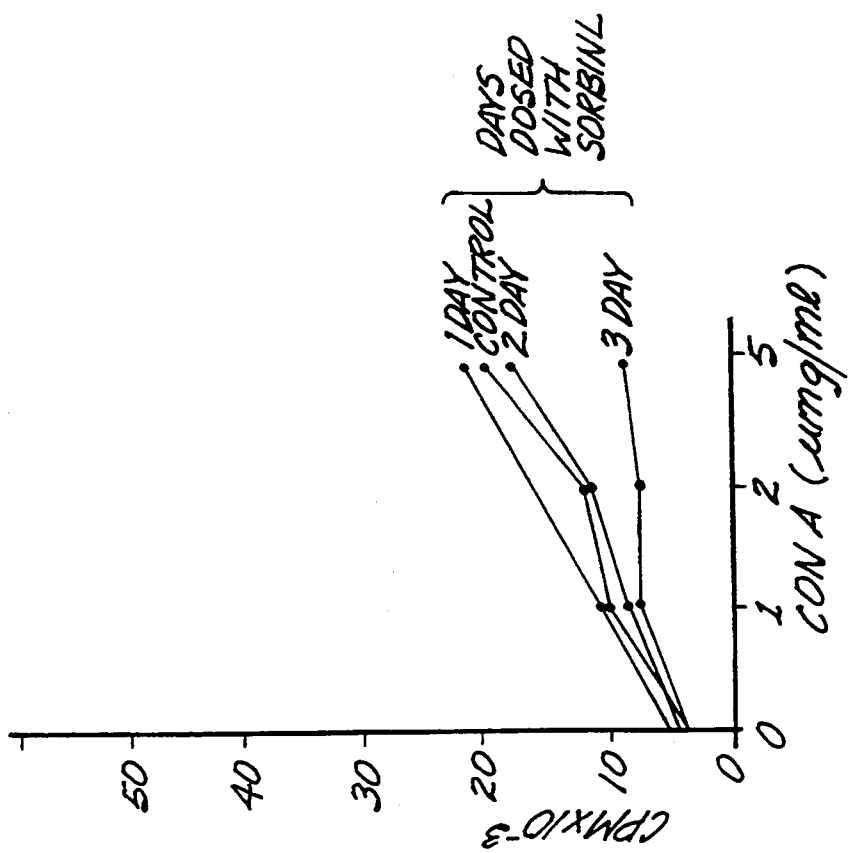
FIG. 21 is another graph which shows that sorbinil inhibits the proliferative response of T-cells to the mitogen Con A, as described in Experiment 8 herein.

The dose response pattern to Con A was also similar in sorbinil-treated and buffer-treated mice, with 2 $\mu$gm/ml of Con A being most effective in cultures harvested on day three (FIG. 20), and 5 $\mu$gm/ml being most stimulatory in cultures harvested on day four (FIG. 21).

Although the kinetics and dose response patterns were similar in sorbinil-treated and control groups, mice receiving sorbinil prior to sacrifice exhibited a reduced proliferative response to the mitogen. Referring now to FIG. 20, the data relating to the cultures harvested on day three are summarized: The mice that received sorbinil for one or two days prior to sacrifice, had the most reduced proliferative response at 1 $\mu$mg of Con A/ml, the lowest dose of Con A employed: the proliferative response was reduced in those mice by 25% and 22%, respectively. At optimal doses of Con A (2 $\mu$mg/ml) the reduction was slightly less; 18% and 11%, respectively. Mice receiving sorbinil for three days prior to sacrifice exhibited the most reduced response to Con A stimulation. Although there was a slight enhancement by 9% in the proliferative response at a Con A concentration of 1 $\mu$mg/ml, the proliferative response to 2 and 5 $\mu$mg/ml of CON A were reduced: 30% and 27%, respectively.

FIG. 21, which represents the data obtained from cultures harvested on day four, when the proliferative response to Con A was declining, shows that the proliferative responses of spleen cells from mice treated with sorbinil for three days prior to harvest were reduced 25–58%. This reduction was greater than that observed in cultures from mice receiving sorbinil for two days prior to sacrifice: 5 to 18% reduction. Interestingly, in cultures of spleen cells from mice that had received sorbinil 24 hours prior to sacrifice, the proliferative response was enhanced by 3–30%.

Discussion

The observation that sorbinil exerts the greatest inhibitory effect on the proliferative response to Con A when it has been present in the animal for three days prior to sacrifice suggests that, in the Con A response, sorbinil is affecting the differentiation of a cell necessary for T-cell proliferation. A model consistent with our observation on the mitogen response would have sorbinil blocking the differentiation of a cell population which is rapidly renewed. The increased inhibiting effects observed when sorbinil treatment was carried out three days before spleen cell harvest would indicate that it requires three or more days for the target cell population to be sufficiently depleted so as to maximally impair the proliferative response to Con A.

The effects of sorbinil on the Con A response, which requires the drug to be present for several days, contrasts with our observations that the sorbinil effects on the DTH response were much more immediate. Together, these data indicate that sorbinil is exerting pleiomorphic effects on the immune system.

Fourth Series of Immunological Experiments

Further studies assessed the effects of sorbinil, tolrestat, and WF-3681 on immunoregulation, in comparison with nonsteroidal anti-inflammatory drugs (NSAIDs). The studies summarized here indicate that the aldose reductase inhibitors that have the reactive conformation and inhibit DTH in mice do not alter normal arachidonic acid metabolism through lipooxegenase or cycloxygenase pathways. These are pathways inhibited by NSAIDs. As predicted, tolrestat and WF-3681, like sorbinil, inhibit selective aspects of the cellular and humoral immune systems by a completely new mechanism that may involve receptor sites for these ARI molecules.

Experiment 9

Mouse P338D cells were loaded with $^3$H-arachidonic acid and then stimulated with A23187, in the presence and absence of $10^{-6}$ M/L sorbinil. The assay protocol was as described generally in Henderson, W. R., and S. J. Klebanoff, J. Biol. Chem. 258: 13522–13527, 1983, which is hereby incorporated by reference. Sorbinil had no effect on the release of arachidonic acid metabolites from normal cells stimulated by A23187.

Experiment 10

Human polymorphonuclear leukocytes (PMNs) were used to study LTB4 release, which is known to be involved in inflammation. Aspirin and retinoic acid are known to inhibit LTB4 production. Sorbinil and WF-3681 had no effect on the production of LTB4 by normal human PMNs.

Experiment 11

Human mononuclear cells were studied for superoxide production in culture in the presence and absence of sorbinil. Superoxide production was stimulated in normal cells using the mitogen phorbol myristate acetate (PMA). Concentrations of sorbinil as high as $10^{-5}$ M/L had no effect on the production of superoxide in normal cells.

Experiment 12

Normal mouse thymocytes were tested in culture for the effect of sorbinil on $^3$H-thymidine incorporation in response to stimulation by the mitogen phytohemagglutin (PHA) in the presence of preformed interleukin IL-1 (a mitogen that dramatically enhances the response of immune cells to lectins such as PHA). Concentrations of sorbinil as high as $10^{-6}$ M/L had no effect on the incorporation of $^3$H-thymidine in response to stimulation of normal mouse thymocytes using PHA.

Experiment 13

Thymocytes from animals that were administered sorbinil were tested for incorporation of $^3$H-thymidine when stimulated by concanavalin A (Con A), a potent mitogen. 10 µg/Kg sorbinil was administered orally to mice 6 hours prior to isolation of thymocytes. $^3$H-thymidine incorporation in cells from sorbinil treated animals was nearly one-half that of cells from untreated animals.

Experiment 14

White cell counts were conducted on animals after 4 days of sorbinil treatment. The standard differential blood count assay revealed that cellularity was normal and there were no changes in the normal lymphocyte populations. Sorbinil did not affect the population of white cells in normal animals.

Experiment 15

Mouse peritoneal cells were isolated from normal mice and tested for $^3$H-thymidine incorporation in the presence and absence of sorbinil. Concentrations of sorbinil as high as $10^{-6}$ M/L had no significant effect on $^3$H-thymidine incorporation in vitro, in control cells or cells stimulated using lipolysaccharide (LPS).

Experiment 16

Human monocytes were isolated and tested for adherence in vitro in the presence and absence of sorbinil. Sorbinil concentrations as high as $10^{-6}$ M/L had no effect on the adherence of normal human monocytes in vitro.

Experiment 17

Human macrophages were stimulated using LPS in vitro, and $^3$H-thymidine incorporation was measured. Sorbinil concentrations as high as $10^{-5}$ M/L had no effect on the incorporation of $^3$H-thymidine in normal cells.

Experiment 18

Con A stimulation of $^3$H-thymidine incorporation was measured using thymocytes from normal mice in the presence and absence of sorbinil. Sorbinil concentrations as high as $10^{-5}$ M/L had no effect on the $^3$H-thymidine incorporation stimulated by Con A in thymocytes from normal mice.

Experiment 19

The effect of sorbinil was tested on a mixed lymphocyte response. Sorbinil concentrations as high as $10^{-5}$ M/L had no effect on the mixed lymphocyte response using spleen cells from irradiated C57B6 mice with thymocytes from Balb C mice.

Experiment 20

In vivo, popliteal lymph node assays were conducted on normal Balb C mice. Sorbinil had no effect on the swelling of popliteal lymph nodes in mice injected in the foot pad with cells from C57BL6 mice.

Experiment 21

The effect of sorbinil was tested on ear swelling in response to PMA, a potent stimulator of inflammation caused by activation of the arachidonic acid pathway. Sorbinil had no effect on the swelling of mouse ears in response to PMA. In contrast, nonsteroidal anti-inflammatory drugs (NSAIDs) like aspirin inhibit this response, which does not require activation of the cellular immune system.

Experiment 22

The effects of sorbinil were tested on ear swelling produced by topical application of arachidonic acid. Both oral and topical administration of sorbinil had no effect on swelling. Topical indomethacin, a well-known NSAID, completely inhibited the swelling produced by topical application of arachidonic acid to normal ears of mice.

Experiment 23

TABLE 5 summarizes experiments that were conducted to compare the effects of sorbinil, tolrestat, WF-3681, and various NSAIDs on DTH, using the protocol described above in the First Series of Immunological Experiments. The Table has 4 columns, listing (left to right) each drug tested in column 1, drug concentrations in column 2, relative swelling in column 3, and effectiveness in column 4.

TABLE 5

| compound | concentration | relative swelling (R) | effectiveness (1 - R) (100%) |
|---|---|---|---|
| Sorbinil | 10 μM | 0.30 | 70% |
|  | 6 μM | 0.66 | 34% |
| Sorbinil single dose before challenge | 6 μM | 0.68 | 32% |
| Sorbinil single dose after challenge | 6 μM | 0.61 | 39% |
| WF-3681 | 6 μM | 0.68 | 32% |
|  | 4.25 μM | 0.62 | 39% |
|  | 2.125 μM | 0.96 | 4% |
| Tolrestat | 6 μM | 0.71 | 29% |
|  | 4 μM | 0.73 | 27% |
|  | 2 μM | 0.79 | 21% |
| Quercitrin | 3 μM | 0.98 | 2% |
| Acetaminophen | 8.5 μM | 1.0 | 0** |
| Ibuprofen | 8.5 μM | 1.0 | 0 |
| Aspirin | 8.5 μM | 1.0 | 0 |

**0 = no effect

The Table shows that the NSAIDs (quercitrin, acetaminophen, ibuprofen, and aspirin) are not effective in preventing DTH, as measured by ear swelling. In contrast, sorbinil, WF-3681, and tolrestat had nearly identical effectiveness on DTH (about 30%, at 6 μM). Furthermore, sorbinil was effective, as a single dose, when administered either before or after the antigenic challenge. Sorbinil, WF-3681, and tolrestat are chemically distinct reagents whose three-dimensional structures all contain the reactive conformation shown in FIGS. 1, 2, and 3.

Referring to TABLES 2 and 5, all the reagents that were shown to exhibit the reactive conformation were also found to inhibit DTH. All the reagents that did not fit the model, e.g., aspirin, failed to inhibit DTH. It is thus proposed that the three-dimensional structure of sorbinil, tolrestat, and WF-3681, and other immunoregulatory agents having the three-dimensional conformation of the disclosed model, precisely fit a naturally occurring site that regulates the immune system. The identity of this natural regulator, which is implicated in mediating the unique type of immunoregulation described above, is presently unknown.

While the present invention has been described in conjunction with preferred embodiments and specific examples, one of ordinary skill after reading the foregoing specification will be able to effect various changes, substitutions of equivalents, and other alterations to the methods and compositions set forth herein. It is therefore intended that the protection granted by Letters Patent hereon be limited only to the definition contained in the appended claims and equivalents thereof.

The embodiments of the invention in which an exclusive property or privilege is claimed are defined as follows:

1. A method of regulating the immune system of a mammalian host, comprising the step of administering to the host a compound having an immunoregulatory conformation comprising an aromatic ring associated with two atoms $X_1$ and $X_2$ selected individually from among oxygen, sulfur, and nitrogen, the immunoregulatory conformation being defined as follows:

$$3.1 \text{ Å} \leq D_1 \leq 4.1 \text{ Å},$$

$$2.4 \text{ Å} \leq D_2 \leq 2.8 \text{ Å},$$

$$3.8 \text{ Å} \leq D_3 \leq 4.2 \text{ Å},$$

and $$35° \leq \alpha° \leq 60°,$$

wherein
 P1 = the plane defined by the aromatic ring,
 $D_1$ = the distance between the centers of plane $P_1$ and atom $X_1$,
 $D_2$ = the distance between the centers of plane $P_1$ and atom $X_2$,
 $D_3$ = the distance between the centers of atoms $X_1$ and $X_2$,
 P2 = the plane defined by atoms $X_1$ and $X_2$ and the center of plane $P_1$, and
 $\alpha°$ = the angle between planes $P_1$ and $P_2$, taken at the intersection of vectors normal to each plane,
wherein the aromatic ring is essentially planar and consists of 5 to 7 ring atoms that are cylindrically symmetrical within about 15 degrees of planar, and
wherein the compound is selected from the group consisting of compounds having the formula:

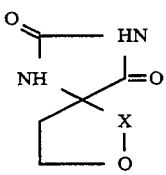

and the base salts thereof with pharmacologically acceptable cations, wherein X is:

benz-α,β-O or substituted benz-α,β-O of the formula:

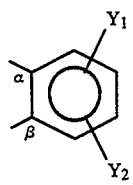

wherein $Y_1$ is hydrogen and $Y_2$ is hydrogen, hydroxy, fluorine, chlorine, lower alkyl or lower alkoxy (each having from one to four carbon atoms), or $Y_1$ and $Y_2$, when taken separately, are each chlorine, lower alkyl or lower alkoxy, and when taken together are —$OCH_2(CH_2)_nO$—, and n is zero or one;

substituted benz-$\alpha,\beta$-O of the formula:

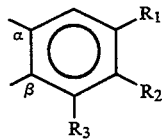

wherein $R_1$ is chlorine, bromine, fluorine, or alkyl of one to three carbon atoms, one of $R_2$ and $R_3$ is hydrogen, and the other of $R_2$ and $R_3$ is amino, monoalkylamino or dialkylamino, wherein each alkyl group has from one to three carbon atoms;

phenyl or phenoxy substituted benz-$\alpha,\beta$-O of the formula:

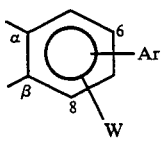

wherein W is hydrogen, methyl, methoxy, phenyl, phenoxy, fluorine, chlorine, or boron at the 6 or 8 position, and Ar is phenyl or phenoxy at the 6 or 8 position;

naph-$\alpha,\beta$-O of the formula:

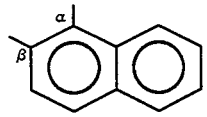

substituted naph-$\alpha,\beta$-O having one or two identical substituents selected from methyl, chlorine, or bromine; or anthracen-$\alpha,\beta$-O of the formula:

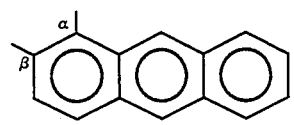

2. The method of claim 1, wherein the aromatic ring is cylindrically symmetrical within about 7 degrees or less of planar.

3. The method of claim 1, wherein the aromatic ring is selected from the group consisting of benzene, pyridine, furan, and thiophene.

4. The method of claim 1, wherein the aromatic ring is part of a ring complex selected from the group consisting of naphthalene and anthracene.

* * * * *

UNITED STATES PATENT AND TRADEMARK OFFICE
CERTIFICATE OF CORRECTION

PATENT NO. : 5,340,829
DATED : August 23, 1994
INVENTOR(S) : Clark et al.

Page 1 of 4

It is certified that error appears in the above-identified patent and that said Letters Patent is hereby corrected as shown below:

| COLUMN | LINE | | |
|---|---|---|---|
| [56] Pg. 1, Col. 1 | Refs. Cited (Publs.) | "Suppl. p. 12" should/read --Suppl., p. 12-- | |
| [56] Pg. 1, Col. 2 | Refs. Cited (Publs.) | "anti- -allergy" should/read --anti-allergy-- | |
| [56] Pg. 1, Col. 2 | Refs. Cited (Publs.) | "$C_{11}H_9FN_2O_3$,*Acta*" should/read --$C_{11}H_9FN_2O_3$, *Acta*-- | |
| [56] Pg. 1, Col. 2 | Refs. Cited (Publs.) | "3-2,-" should/read --3-(2,--- | |
| [56] Pg. 2, Cols. 1 & 2 | Refs. Cited (Publs.) | "anti-r-heumatic" should/read --anti-rheumatic-- | |
| 5 | 10 | "the α° intersection" should/read --the intersection-- | |
| 5 | 67 | After "Sorbinil", "IR" should/read --*IR*-- | |
| 5 | 68 | After "ARI", "AC" should/read --*AC*-- | |
| 6 | 16 | After "Tolrestat", "IR" should/read --*IR*-- | |
| 6 | 18 | After "WF-3681", "IR" should/read --*IR*-- | |
| 6 | 21 | "ocher" should/read --other-- | |

UNITED STATES PATENT AND TRADEMARK OFFICE
CERTIFICATE OF CORRECTION

PATENT NO. : 5,340,829
DATED : August 23, 1994
INVENTOR(S) : Clark et al.

It is certified that error appears in the above-identified patent and that said Letters Patent is hereby corrected as shown below:

| COLUMN | LINE | |
|---|---|---|
| 7 | 50 | "the a for" should/read --the $\alpha°$ for-- |
| 8 | 37 | "oxygen 0$_4$" should/read --oxygen $O_4$-- |
| 8 | 39 | "0$_4$" should/read --$O_4$-- |
| 9-10 | 1-17 | Formula 1 should read: |

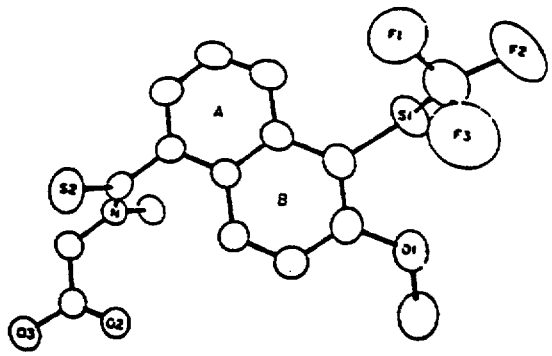

UNITED STATES PATENT AND TRADEMARK OFFICE
CERTIFICATE OF CORRECTION

PATENT NO. : 5,340,829   Page 3 of 4

DATED : August 23, 1994

INVENTOR(S) : Clark et al.

It is certified that error appears in the above-identified patent and that said Letters Patent is hereby corrected as shown below:

| COLUMN | LINE | |
|---|---|---|
| 9-10 | 26-48 | Formula 2 should read: |

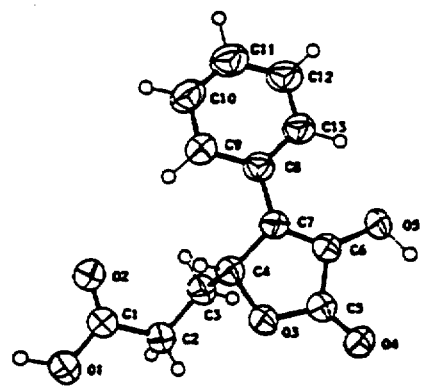

UNITED STATES PATENT AND TRADEMARK OFFICE
CERTIFICATE OF CORRECTION

PATENT NO. : 5,340,829
DATED : August 23, 1994
INVENTOR(S) : Clark et al.

It is certified that error appears in the above-indentified patent and that said Letters Patent is hereby corrected as shown below:

| | | |
|---|---|---|
| 9 | 51 | "$O_2$," should/read --$O_2$,-- |
| 9 | 52 | "$O_4$." should/read --$O_4$.-- |
| 11 | 26 | "$Y_2$ when" should/read --$Y_2$, when-- |
| 19 | 58 | "J. Exp. Wed." should/read --J. Exp. Med.-- |
| 20 | 20 | "18" should/read --18-- |
| 24 | 38 | "P1" should/read --P1-- |

Signed and Sealed this

Twenty-first Day of February, 1995

Attest:

BRUCE LEHMAN

*Attesting Officer*   *Commissioner of Patents and Trademarks*